US011098036B2

(12) United States Patent
Li et al.

(10) Patent No.: US 11,098,036 B2
(45) Date of Patent: Aug. 24, 2021

(54) CATALYST-FREE AND REDOX-NEUTRAL INNATE TRIFLUOROMETHYLATION AND ALKYLATION OF (HETERO)AROMATICS ENABLED BY LIGHT

(71) Applicant: THE ROYAL INSTITUTION FOR THE ADVANCEMENT OF LEARNING/MCGILL UNIVERSITY, Montréal (CA)

(72) Inventors: Chao-Jun Li, Brossard (CA); Wenbo Liu, Ann Arbor, MI (US); Peng Liu, Wuhan (CN)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 0 days.

(21) Appl. No.: 16/649,269

(22) PCT Filed: Sep. 28, 2018

(86) PCT No.: PCT/CA2018/051223
§ 371 (c)(1),
(2) Date: Mar. 20, 2020

(87) PCT Pub. No.: WO2019/060998
PCT Pub. Date: Apr. 4, 2019

(65) Prior Publication Data
US 2020/0216430 A1 Jul. 9, 2020

Related U.S. Application Data

(60) Provisional application No. 62/565,365, filed on Sep. 29, 2017.

(51) Int. Cl.
| | |
|---|---|
| *C07D 413/12* | (2006.01) |
| *C07C 315/04* | (2006.01) |
| *C07C 317/24* | (2006.01) |
| *C07D 207/33* | (2006.01) |
| *C07D 209/10* | (2006.01) |
| *C07D 215/48* | (2006.01) |
| *C07D 219/02* | (2006.01) |
| *C07D 221/10* | (2006.01) |
| *C07D 233/64* | (2006.01) |
| *C07D 277/64* | (2006.01) |
| *C07D 311/30* | (2006.01) |
| *C07D 401/04* | (2006.01) |
| *C07D 401/12* | (2006.01) |
| *C07D 473/12* | (2006.01) |
| *C07H 19/067* | (2006.01) |
| *C07H 19/073* | (2006.01) |
| *C07D 473/00* | (2006.01) |

(52) U.S. Cl.
CPC .......... *C07D 413/12* (2013.01); *C07C 315/04* (2013.01); *C07C 317/24* (2013.01); *C07D 207/33* (2013.01); *C07D 209/10* (2013.01); *C07D 215/48* (2013.01); *C07D 219/02* (2013.01); *C07D 221/10* (2013.01); *C07D 233/64* (2013.01); *C07D 277/64* (2013.01); *C07D 311/30* (2013.01); *C07D 401/04* (2013.01); *C07D 401/12* (2013.01); *C07D 473/00* (2013.01); *C07D 473/12* (2013.01); *C07H 19/067* (2013.01); *C07H 19/073* (2013.01)

(58) Field of Classification Search
None
See application file for complete search history.

(56) References Cited

U.S. PATENT DOCUMENTS 6,215,021 B1 * 4/2001 Shreeve ................ C07C 381/12
562/30

FOREIGN PATENT DOCUMENTS

| JP | 2017075120 A | * | 4/2017 | ........... C07C 317/24 |
| WO | WO-2015000076 A9 | * | 8/2015 | ........... C07C 269/06 |

OTHER PUBLICATIONS

Hendrickson et al. ("Triflones (CF3SO2C). A Survey of Reactivity and Synthetic Utility", Journal of the American Chemical Society, 96:7, Apr. 1974, pp. 2275-2276).*
Arimori et al. (Royal Society Open Science, 3, 160102, Apr. 2016, pp. 1-9).*
Liu et al. ("Oxysulfonylation of Alkenes with Sulfonyl Hydrazides under Transition-Metal-Free Conditions", European Journal of Organic Chemistry, Jan. 2016, pp. 910-912).*
Gong et al. ("Synthesis of β-Keto Sulfones via Coupling of Aryl/Alkyl Halides, Sulfur Dioxide and Silyl Enolates through Metal-Free Photoinduced C-X Bond Dissociation", Advanced Synthesis and Catalysis, Sep. 2017, vol. 359, Issue 17, pp. 2999-3004). (Year: 2017).*
Jiang et al. ("Sulfonation and Trifluoromethylation of Enol Acetates with Sulfonyl Chlorides Using Visible-Light Photoredox Catalysis", European Journal of Organic Chemistry, Aug. 2013, vol. 2013, Issue 24, pp. 5485-5492). (Year: 2013).*

(Continued)

*Primary Examiner* — Rosalynd A Keys
(74) *Attorney, Agent, or Firm* — Norton Rose Fulbright Canada LLP

(57) ABSTRACT

The present disclosure relates to reagents and method for performing trifluoromethylation, difluoromethylation or alkylation of aromatic or heteroaromatic rings in a redox-neutral manner without any catalyst which are enabled by light. In addition, there are methods for synthesizing the starting reagents used in the trifluoromethylation, difluoromethylation or alkylation reactions.

12 Claims, No Drawings

(56) References Cited

OTHER PUBLICATIONS

Pan et al. ("An efficient electrochemical synthesis of β-keto sulfones from sulfonates and 1, 3-dicarbonyl compounds", Tetrahedron, Aug. 2015, vol. 71, Issue 34, pp. 5525-5530). (Year: 2015).*
Loghmani-Khouzani et al. ("α-Fluorination of β-ketosulfones by Selectfluor™ F-TEDA-BF4", Tetrahedron, Jul. 2008, vol. 64, Issues 30-31, pp. 7419-7425). (Year: 2008).*
Grossert et al. ("Steric effects in the diastereoselective reduction of β-ketosulfones", Canadian Journal of Chemistry, Nov. 1988, vol. 66, No. 11, pp. 2860-2869). (Year: 1988).*
Chen, Y. et al. "Elaboration of 2-(Trifluoromethyl)indoles via a Cascade Coupling/Condensation/Deacylation Process". Org. Lett. vol. 10, No. 4, 2008, pp. 625-628.
Eugene, F. et al. "Improved synthesis of trifluormethyl sulfones used as intermediates for the preparation of di- or tri-substitued olefins". J. Fluor. Chem. 66 (1994) pp. 301-309.
Fang, Y-Q. and Lautens, M. "Pd-Catalyzed Tandem C—N/C—C Coupling of gem-Dihalovinyl Systems: A Modular Synthesis of 2-Substituted Indoles". Org. Lett. 2005, vol. 7, No. 16. pp. 3549-3552.
Hsieh, J-C. and Cheng, C-H. "O-Dihaloarenes as aryne precursors for nickel-catalyzed [2+2+2] cycloaddition with alkynes and nitriles". Chem. Commun., 2008. pp. 2992-2994.
Hwang, C. et al. "Base-promoted, deborylative secondary alkylation of N-heteroaromatic N-oxides with internal gem-bis[(pinacolato)boryl]alkanes: a facile derivatization of 2,2'-bipyridyl analogues". Chem. Commun., 2017, 53, pp. 7573-7576.
Ji, Y. et al. "Innate C—H trifluoromethylation of heterocycles". Proc. Natl Acad. Sci. USA 2011, 108, 14411, pp. 1-5.
Kobayashi, Y. et al. "Studies on Organic Fluorine Compounds. Part 35. Trifluoromethylation of Pyrimidine- and Purine-nucleosides with Trifluoromethyl-Copper Complex". J. Chem. Soc., Perkin Trans. 1 1980, 2755-2761.
Li, L. et al. "Simple and Clean Photoinduced Aromatic Reaction". J. Am. Chem. Soc. 2016, 138. pp. 5809-5812.
Liu, P. et al. "Catalyst-Free and Redox-Neutral Innate Trifluoromethylation and Alkylation of Aromatics Enabled by Light". J. Am. Chem. Soc. 2017, 139. pp. 14315-14321.
Molander, G. A. et al. "Direct Alkylation of Heteroaryls Using Potassium Alkyl- and Alkoxymehtyltrifluoroborates". Org. Lett. 2011, vol. 13, pp. 1852-1855.
Nagib, D. A. and MacMillan, D.W.C. "Trifluoromethylation of arenes and heteroarenes by means of photoredox catalysis". Nature, 2011, vol. 480, pp. 224-228.
Paul, S. and Guin, J. "Dioxygen-Mediated Decarbonylative C—H Alkylation of Heteroaromatic Bases with Aldehydes". 'Chem. Eur. J. 2015, 21, pp. 17618-17622.
Rueping, M. and Ieawsuwan, W. "A Manganese-Catalyzed Cross-Coupliing Reaction". Synlett 2007, No. 2, pp. 247-250.
Seo, S. et al. "Silver-catalysed trifluoromethylation of arenes at room temperature". Chem. Commun. 2013, 49, pp. 6385-6387.
Shan, G. et al. "A Facile Synthesis of Substituted 2-Alkylquinolines through [3+3] Annulation between 3-Ethoxycyclobutanones and Aromatic Amines at Room Temperature". Org. Lett. 2011, vol. 13, pp. 5770-5773.
Stanek, K. et al. "Reactivity of a 10-I-3 Hypervalent Iodine Trifluoromethylation Reagent With Phenols". J. Org. Chem. 2008, 73, pp. 7678-7685.
Wang, D. et al. "Catalyst-free Direct C—H Trifluoromethylation of Arene in Water-Acetonitrile". Green Chem. 2016, 18, 5967, pp. 1-5.
Wiehn, M. S. et al. "Electrophilic trifluoromethylation of arenes and N-heteroarenes using hypervalent idodine reagents". J. Fluor. Chem., 131, (2010) pp. 951-957.
Ye, Y. et al. "Silver-Mediated Trifluoromethylation of Arenes Using TMSCF3". Org. Lett. 2011, vol. 13, No. 20. pp. 5464-5467.

* cited by examiner

CATALYST-FREE AND REDOX-NEUTRAL INNATE TRIFLUOROMETHYLATION AND ALKYLATION OF (HETERO)AROMATICS ENABLED BY LIGHT

The present application is the 371 national phase entry of PCT/CA2018/051223 filed Sep. 28, 2018, the content of which is hereby incorporated in its entirety. The present application also claims priority from U.S. provisional patent application Ser. No. 62/565,365, filed Sep. 29, 2017 and entitled "CATALYST-FREE AND REDOX-NEUTRAL INNATE TRIFLUOROMETHYLATION AND ALKYLATION OF (HETERO)AROMATICS ENABLED BY LIGHT", the disclosure of which is hereby incorporated by reference in its entirety.

FIELD OF THE DISCLOSURE

The present disclosure relates to reagents and method for performing trifluoromethylation, difluoromethylation, or alkylation of aromatic or heteroaromatic rings.

BACKGROUND OF THE DISCLOSURE

The Minisci alkylation is a powerful tool to functionalize aromatics via alkyl radical addition. Complementary to the Friedel-Crafts alkylation, it is particularly effective to functionalize electron-deficient aromatics. The original Minisci protocol employs aliphatic carboxylic acids to generate alkyl radicals through the oxidative decarboxylation. Current approaches to access alkyl radicals consist of two general strategies: (a) the oxidative and (b) the reductive approaches.

In terms of the redox-economy towards more sustainable synthesis, the above-mentioned methods to access alkyl radicals are not satisfying because of the involvement of harsh oxidants and reductants. These redox reagents, often used in superstoichiometric amount, not only impair the substrate scope and evoke the chemo-selectivity issues, but also generate obnoxious by-products especially for large scale synthesis. Therefore, redox-neutral protocols obviating these external oxidizing and reducing reagents are desirable.

SUMMARY OF THE DISCLOSURE

An aspect relates to a compound of formula:

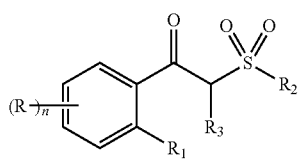
(I)

wherein R1; R2; R3; R and n are as defined herein.

A further aspect relates to the method for forming a compound of formula:

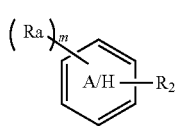
(II)

comprising:
i) mixing together a compound of formula:

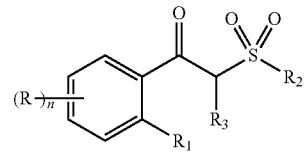
(I)

with compound of formula:

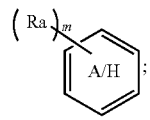
(III)

and
ii) photo irradiating the mixture of step i) to provide said compound of formula (II);
wherein

R1; R2; R3; R, Ra, m and n are as defined herein.

A further aspect relates to a method for forming a compound of formula:

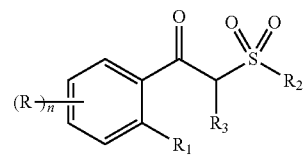
(I)

comprising:
1) reacting a compound of formula

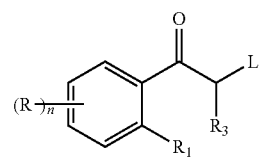
(IV)

with a compound of formula

R2—S—X⁺ (Va)

wherein R1; R2; R3; R, and n are as defined herein;
L is a leaving group
X is a counterion;

to provide a compound of formula

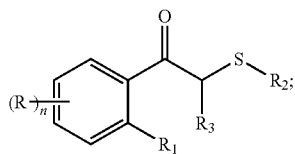
(VI)

wherein R1; R2; R3; R, and n are as defined herein; and
2) reacting said compound of formula (VI) with an oxidant to provide said compound of formula (I); or
3) reacting said compound of formula (IV) with a compound of formula R2-SO$_2^-$X$^+$ (Vb);

wherein R2 and X$^+$ are as defined above, to provide said compound of formula (I).

DETAILED DESCRIPTION OF THE DISCLOSURE

In one embodiment, the compound herein is represented by the formula:

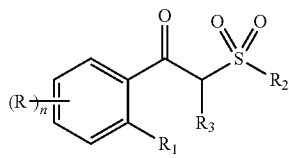
(I)

wherein
R1 is H, or an optional substituent;
R2 is CF$_3$, CF$_2$H, a linear alkyl of 2 or more carbon atoms, a branched alkyl of 3 or more carbon atoms or a cycloalkyl of 3 or more carbon atoms;
R3 is H, or a C1-C6 linear alkyl, C3-C6 branched alkyl or C3-C6 cycloalkyl;
or R1 and R3, together with the atoms to which they are attached, form a 5-6 membered ring; each R is an independently selected from H or an optional substituent;
n is an integer of 1 to 4.

In one embodiment, there is provided the method for forming a compound of formula:

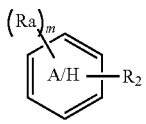
(II)

wherein

defines a mono or polycyclic aryl ring or a mono or polycyclic heteroaryl ring;

each Ra is independently selected from H or an optional substituent;
R2 is CF$_3$, CF$_2$H, a linear alkyl of 2 or more carbon atoms, a branched alkyl of 3 or more carbon atoms or a cycloalkyl of 3 or more carbon atoms; and
m is an integer of 1 to 5;
comprising:
i) mixing together a compound of formula:

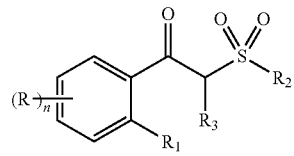
(I)

wherein R1 is H, or an optional substituent;
R2 is as defined above;
R3 is H, or a C1-C6 linear alkyl, C3-C6 branched alkyl or C3-C6 cycloalkyl;
or R1 and R3, together with the atoms to which they are attached, form a 5-6 membered ring;
each R is independently selected from H or an optional substituent;
n is an integer of 1 to 4;
with compound of formula:

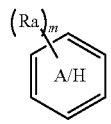
(III)

wherein

is as defined above, and Ra and m are as defined above;
ii) photo irradiating the mixture of step i) to provide said compound of formula (II).

In one embodiment, an acid (such as TFA) is added to the reaction mixture of (I) and (III).

In one embodiment, an acid (such as TFA) is added to the reaction mixture of (I) and (III) when R2 is other CF$_3$, The acid may be an organic or inorganic acid having a suitable pKa. Examples of organic acid include sulfonic acids or carboxylic acids.

In on embodiment of the method herein, in particular for providing a compound of formula II, the photo irradiation is performed at a wavelength of about 200 nm to about 800 nm, alternatively from about 250 nm to about 600 nm and more preferably about 250 to about 400 nm. Typical examples include the use of a 300 W mercury lamp or standard household lamp.

In on embodiment of the method herein, in particular for providing a compound of formula II, the molar ratio of (beta-keto sulfone) compound I to (aryl/heteroaryl) compound (III) can be from about 1 to about 10 equivalents, or preferably about 1 to about 3 equivalents.

In on embodiment of the method herein, in particular for providing a compound of formula II, the reaction can be conducted in most common organic solvent without a detrimental effect on the reaction. A non-limiting list preferably includes acetone, acetonitrile, methanol, and DMSO.

The invention herein allows to perform the introduction of trifluoromethyl, difluoromethylation or alkyl on (hetero) aromatic rings in a redox-neutral manner without any catalyst.

In one embodiment, there is provided the method for forming a compound of formula:

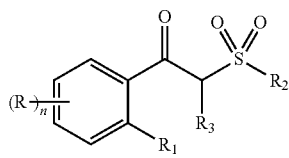

(I)

comprising:
1) reacting a compound of formula

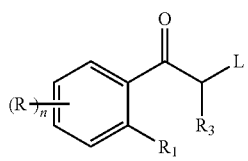

(IV)

with a compound of formula $$R_2\text{—}S^-X^+$$ (V)

wherein R1; R2; R3; R, and n are as defined herein;
L is a leaving group
X is a counterion;
to provide a compound of formula

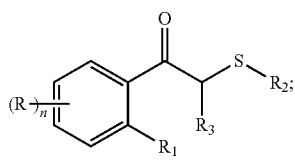

(VI)

wherein R1; R2; R3; R, and n are as defined herein; and reacting said compound of formula (VI) with an oxydant to provide said compound of formula (I).

In one embodiment, there is provided the method for forming a compound of formula (I) as defined above comprising:
1) reacting a compound of formula

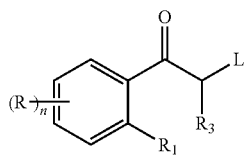

(IV)

with a compound of formula reacting with $$R2\text{-}SO_2\text{-}X^+$$ (Vb)

wherein R1; R2; R3; R, X+, L and n are as defined above; to provide said compound of formula (I).

In one embodiment, R1 and R3, together with the atoms to which they are attached, form a 5 membered ring.

In one embodiment, R1 is H

In one embodiment, the linear alkyl of group R2 is preferably comprising 2 to 10, alternatively 2 to 7 carbon atoms.

Examples of linear alkyl groups include methyl, ethyl, propyl, butyl, pentyl or hexyl.

In one embodiment, the branched alkyl of group R2 is preferably comprising 3 to 8, alternatively 3 to 7 carbon atoms.

Examples of branched alkyl groups include, isopropyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, t-butyl, pentyl, isopentyl, neopentyl, 2-ethyl-1-hexyl.

In one embodiment, the cycloalkyl of group R2 is preferably comprising 3 to 8, alternatively 3 to 6 carbon atoms.

Examples of cycloalkyl groups include cyclopropyl, cyclobutyl, cyclopentyl and cyclohexyl.

In one embodiment, R2 is $CF_3$.
In one embodiment, R2 is $CF_2H$.
In one embodiment, R3 is H, or a C1-C6 linear and branched alkyl.
In one embodiment, R3 is H, or a methyl.

In one embodiment, the optional substituent (R or Ra): is halogen, C1-6alkyl, C2-6alkenyl, C1-6 alkoxy, substituted C1-6 alkoxy, substituted C1-6 alkoxy aryl, oxo (C═O), cyano (CN), —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl; Examples of cycloalkyls include C3 to C6 alkyl, such as cyclopropyl, cyclobutyl, cyclopentyl and cyclohexyl.

In one embodiment, the optional substituent R is H or C1-6alkyl.

In one embodiment, the optional substituent R is H.

In one embodiment, the optional substituent Ra is H, C1-6alkyl, C1-6 alkoxy, aryl, hydroxyl, or —C(O)OR40 wherein R40 and R41 are each independently H, or C1-6alkyl;

In one embodiment, the compound herein is represented by the formula:

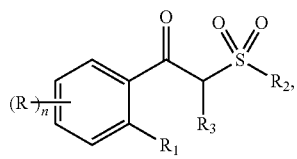

wherein
R1 is H;
R2 is $CF_3$, $CF_2H$, a linear alkyl of 2 or more carbon atoms (in particular 2 to 7 carbon atoms), a branched alkyl of 3 or more carbon atoms (in particular 3 to 7 carbon atoms) or a cycloalkyl of 3 or more carbon atoms (in particular 3 to 6 carbon atoms); R3 is C1-C6 linear alkyl;

or R1 and R3, together with the atoms to which they are attached, form a 5-6 membered ring; each R is H.

The term "aryl" represents a carbocyclic moiety containing at least one monocyclic (preferably a 6 membered monocyclic) or polycyclic (preferably 9-10 membered bicyclic) benzenoid-type ring, which may be optionally substituted with one or more substituents. An example of aryl is a phenyl ring.

The term "heteroaryl" is meant to include monocyclic (preferably 5-6 membered) or a polycyclic (preferably 9-10 membered fused-bicyclic or 12-14 membered fused tricyclic) rings, wherein said ring(s) is(are) interrupted by at least one heteroatom selected from oxygen (O), sulfur (S) or nitrogen (N). The "heteroaryl" is also optionally substituted by one or more substituents.

Examples of heteroaryl groups include

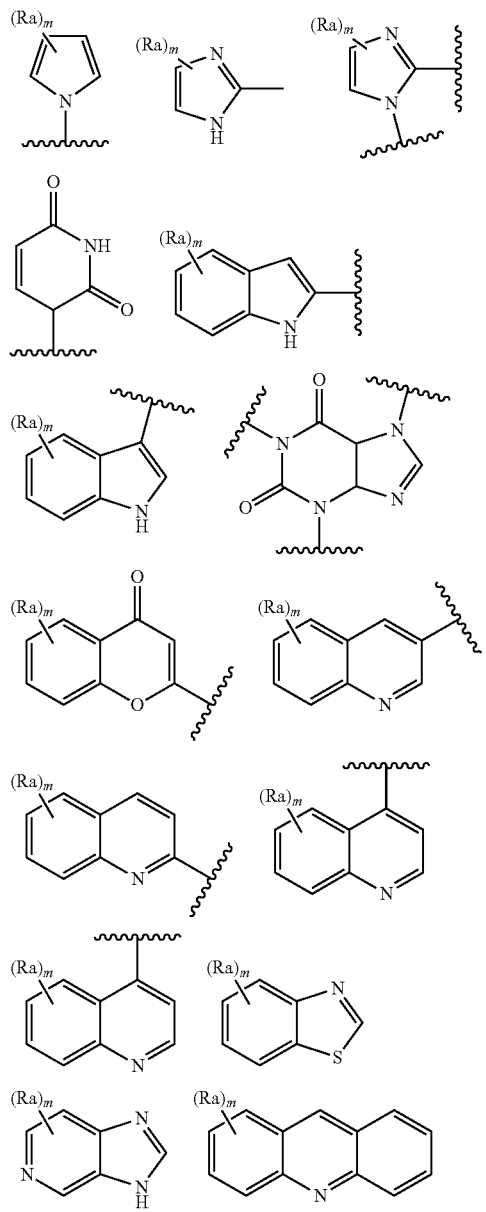

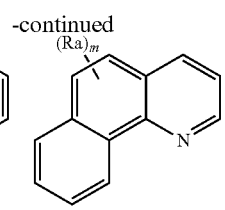

-continued

In one embodiment, the optional substituent (R or Ra): is halogen, C1-6alkyl, C2-6alkenyl, C1-6 alkoxy, aryl, oxo (C=O), cyano (CN), —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl;

Examples of cycloalkyls include C3 to C6 alkyl, such as cyclopropyl, cyclobutyl, cyclopentyl and cyclohexyl.

In one embodiment, the optional substituent R is H or C1-6alkyl.

In one embodiment, the optional substituent R is H.

In one embodiment, the optional substituent Ra is H, C1-6alkyl, C1-6 alkoxy, aryl, hydroxyl, or —C(O)OR40 wherein R40 and R41 are each independently H, or C1-6alkyl; The term "counterion" is meant to include an ion that accompanies an ionic species (e.g. in this present invention the species R2-S$^-$) in order to maintain electric neutrality. The skilled person in the art can select the appropriate counterion so that it is not causing a detrimental effect to the reaction with compound of formula (IV). Examples of counterion includes: Na$^+$, Li$^+$, K$^+$, and NH$_4^+$.

The term "leaving group" is not particularly limited and include any leaving group known to those of ordinary skills in to art and can be displaced by the species R2-S$^-$. The leaving group can be a halide such as Cl—, Br—, and I—, and sulfonate esters such as tosylate (TsO$^-$), and triflate (TfO$^-$).

Examples

General Experimental Procedures

All the reactions were carried out under argon atmosphere using standard Schlenk technique. $^1$H NMR (500 MHz), $^{19}$F NMR (471 MHz) and $^{13}$C NMR (126 MHz) were recorded on a NMR spectrometer with CDCl$_3$ as the solvent. Chemical shifts of $^1$H, $^{19}$F and $^{13}$C NMR spectra are reported in parts per million (ppm). The residual solvent signals were used as references and the chemical shifts were converted to the TMS scale (CDCl$_3$: δ H=7.26 ppm, δ C=77.16 ppm). All coupling constants (J values) were reported in Hertz (Hz). High-resolution mass spectrometry was conducted through using atmospheric pressure chemical ionization (APCI) or electro-spraying ionization (ESI), and was performed at McGill University on a Thermo-Scientific Exactive Orbitrap. Protonated molecular ions [M+H]$^+$ or sodium adducts [M+Na]$^+$, were used for empirical formula confirmation. Column chromatography was performed on silica gel 200-300 mesh.

General Procedures for the Synthesis of Trifluoromethylation Reagents

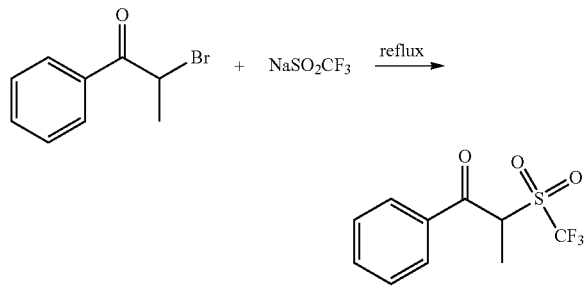

Under argon, sodium triflinate (2.94 g, 18.8 mmol), DMA (15 mL) and 2-bromo-1-phenylpropan-1-one (2.0 g, 9.4 mmol) were added into a 50 mL round bottom flask fitted with a reflux condenser and a magnetic stir bar. The stirred reaction mixture was then heated under argon at 70° C. for 12 h. After the reaction, 30 mL water was added. The resulting mixture was extracted with 20 mL diethyl ether for three times. The ethereal phase was then washed twice with 15 mL water and dried over magnesium sulfate. The resulting solution was concentrated via rotary evaporation, and the residue was purified by column chromatography on silica gel to provide the desired product 14.

General Procedures for Trifluoromethylation of Aromatics

Arenes or heteroarenes (0.1 mmol) and 14 (0.15-0.3 mmol) were added into 0.5 mL acetonitrile. The air-tight quartz tube (10 mL) containing these reactants and solvent was evacuated by three frozen-pump-thaw cycles and back-filled with argon prior to use. The reaction was stirred at 20° C. under photo irradiation by using either a 300 W xenon lamp or two 45 W household CFLs. In the case of 300 W xenon lamp (Figure S1, left picture), the air-tight quartz flask needs to be placed into a big jacketed quartz container full of cold water, which can keep the reaction temperature around 20° C. under strong photo-irradiation. After the reaction, the resulting crude mixture was purified by flash chromatography on silica gel to provide the desired product.

General Procedures for Synthesizing Difluoromethylating Reagents

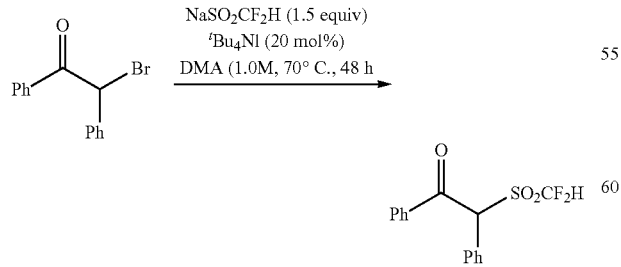

To a 25 mL Schrenk tube charged with a teflon-coated magnetic stirring bar was added sodium difluoromethane-sulfinate (NaSO$_2$CF$_2$H, 2.48 g, 18.0 mmol, 1.5 equiv), tetrabutylammonium iodide (0.36 g, 2.4 mmol, 20 mol %) and 2-bromo-1,2-diphenylethan-1-one (3.30 g, 12 mmol, 1.0 equiv). After that, the reaction system was evacuated and back-filled with argon for degas purpose. This cycle was repeated for three times to ensure the inert atmosphere (reaction under ambient conditions is not tested). The stirred mixture was heated at 70° C. for 48 hours. After the reaction, the resulted mixture was poured into 30 mL water and extracted with 20 mL diethyl ether for three times. The organic phase was then washed twice with 15 mL water, dried over MgSO$_4$, concentrated on rotary evaporation. The residue was purified by column chromatography on silica gel to provide the desired product (3.54 g, 95%, 11.4 mmol).

General Procedures for Difluoromethylation of Aromatics

The preparation of 1b is representative and applicable to all CF$_2$H-containing compounds synthesis in this work unless otherwise specified. To an air-tight quartz tube (10.0 mL) equipped with a teflon-coated magnetic stirring bar was added the caffeine 1a (0.10 mmol, 1.0 equiv), 2-((difluoromethyl)sulfonyl)-1,2-diphenylethan-1-one (0.40 mmol, 4.0 equiv). Shortly after, anhydrous CH$_3$CN (0.50 mL, 0.20 M) pre-dried over 4 Å molecular sieves (beads, 8-12 mesh) was injected, followed by trifluoroacetic acid (TFA, 2.0 mmol, 20.0 equiv, 153 μL). The resulting mixture was evacuated by three freeze-pump-thaw cycles and back-filled with ultra-purified argon (>99.999%).

The air-tight quartz flask was placed into a jacketed quartz container cooled equipped with WK 300 LAUDA chiller (The water circulation would maintain reaction temperature around 30° C.). The reaction was stirred at room temperature under photo-irradiation by 300 W Xenon lamp for 12 hours.

The reaction was quenched by saturated NaHCO$_3$ solution and supplemented with H$_2$O to get 5.0 mL mixture. The mixture was extracted with diethyl ether (5.0 mL×3). The combined ethereal solution was washed with H$_2$O, and brine, then dried over Na$_2$SO$_4$, concentrated on rotary evaporation. The residue was purified by either column chromatography on silica gel or preparative thin layer chromatography to provide the desired product 1b.

General Procedures for the Synthesis of Alkylation Reagents

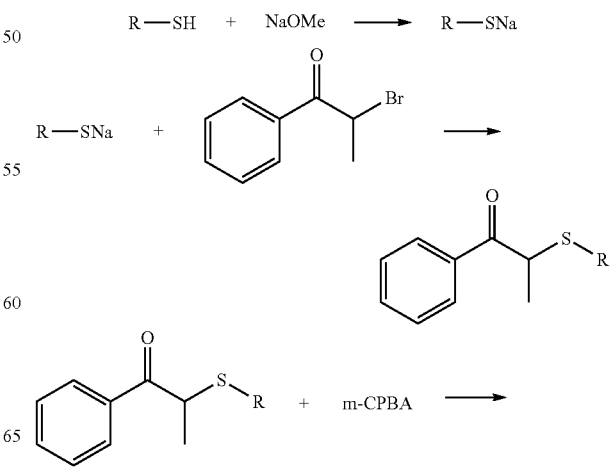

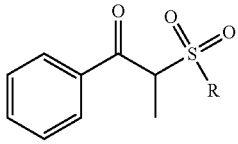

Sodium methoxide (1.14 mL, 4.4 M in methanol, 5 mmol) and 2-propanethiol (0.36 g, 4.7 mmol) was added slowly to 10 mL methanol under argon atmosphere at 0° C. The ice-bath was removed and it was stirred for 20 min at r.t. 2-bromo-1-phenylpropan-1-one (1.0 g, 4.7 mmol) was then added dropwise to the above mixture at r.t. and the reaction mixture was heated at 80° C. for 1 h. The reaction mixture was allowed to cool down to r.t., and methanol was evaporated and the crude slurry was extracted with ether (3×30 mL), washed with water, brine, dried over $Na_2SO_4$, and concentrated. The residue was dissolved in $CH_2Cl_2$ (15 mL), and m-CPBA (77% effective ingredient, 2.1 g, 9.4 mmol) was added slowly under argon. The reaction was monitored by TLC. After approximately 90 min., the mixture was filtered and washed with $CH_2Cl_2$. The resulting solution was washed with $H_2O$, $NaHCO_3$ (1 M), and brine, then dried over $MgSO_4$. The solution was concentrated via rotary evaporation, and the residue was purified by column chromatography on silica gel to provide the desired product 36.

General Procedures for Alkylation of Aromatics

Heteroarenes (0.1 mmol) and 36 (0.12 mmol) were added into a 5 mL quartz tube with a Teflon-coated stir bar. 0.5 mL acetone was added into the above quartz tube successively to produce a clear solution. Following that, TFA (2 mmol) was added into the above clear solution. After capped, the air-tight quartz tube containing these reactants and solvent was evacuated by three frozen-pump-thaw cycles and back-filled with argon prior to use. The reaction was stirred at 80° C. under photo irradiation by using a 300 W mercury lamp (Figure S1, right picture). After 12 h, saturated $NaHCO_3$ solution was added. The mixture was extracted with ethyl acetate. The resulting solution was washed with $H_2O$, and brine, then dried over $MgSO_4$. The solution concentrated via rotary evaporation, and the residue was purified by column chromatography on silica gel to provide the desired product.

To utilize light to homolytically generate alkyl radical in a synthetically useful way the following criteria are desirable: 1) the undesired twin radical is less reactive than the target alkyl radical; 2) the reversible reaction of homolytic cleavage should be inferior to the desired Minisci alkylation.

Applicant has surprisingly found that these requirements can be met when the undesired radical is also a carbon radical because: 1) since they are both carbon radicals, the target alkyl radical would at least bear a comparable reactivity with the undesired carbon radical; 2) the reactivity of the undesired carbon radical could be further diminished through modulating its electronics and sterics.

Applicant has found that by using a stabilized substituent the regioselectivity issue can be solved: 1) the α-cleavage would prefer the pathway to produce the more stable dummy radical $R^1$, which generates the desired radical in a more selective way; 2) the more stable dummy radical $R^1$ is less reactive, which could not compete with the target radical to react with the aromatics and the desired Minisci product would prevail.

Trifluoromethylation.

Applicant has found that trifluoromethylation of aromatics and heteroaromatic rings is possible when using the invention disclosed herein. Such compounds are important in pharmaceutical industry and material chemistry.

Applicant has used in Table 1, a representative number trifluoromethyl compounds, both as comparative compounds and compounds disclosed in accordance with the present disclosure. 1,3,5-trimethoxybenzene was selected as the substrate to perform trifluoromethylation. Under light irradiation, comparative compounds 1-6 did not produce any product and comparative compound 7 only delivered the product in 9% yield. Similarly, comparative compounds 8, 9 and 10 having a trifluoromethyl sulfone group failed to provide satisfactory results. Aryl methyl ketones (11-14) in accordance with the invention, provided a surprisingly satisfactory of the desired trifluoromethyl product.

Without being bound to theory, the inventors believe that the reactivity of the compounds in accordance with the invention is attributed to the stabilizing effect of both carbonyl (and methyl groups—R3 when present) as well as the steric bulkiness. The stabilizing effect implies the ease to undergo the homolytic cleavage and the bulky environment implies its lower capacity to react with the aromatic than with trifluoromethyl radical.

TABLE 1

Evaluations of trifluoromethyl compounds (a)

TABLE 1-continued

Evaluations of trifluoromethyl compounds (a)

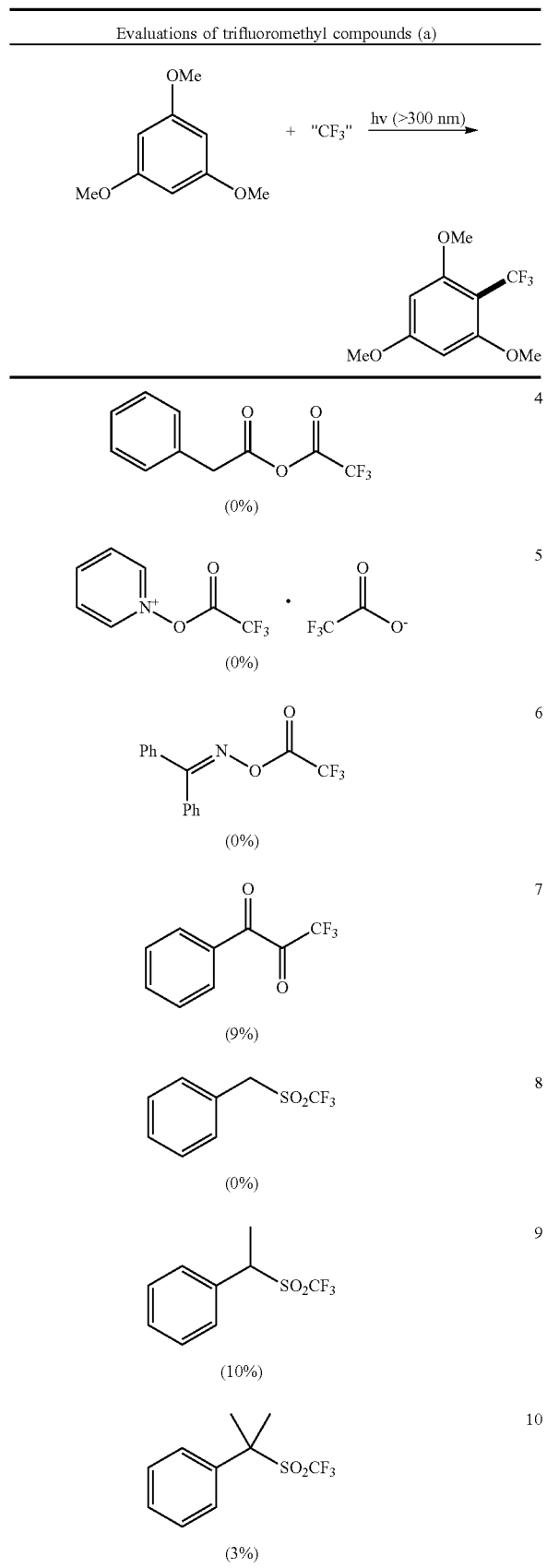

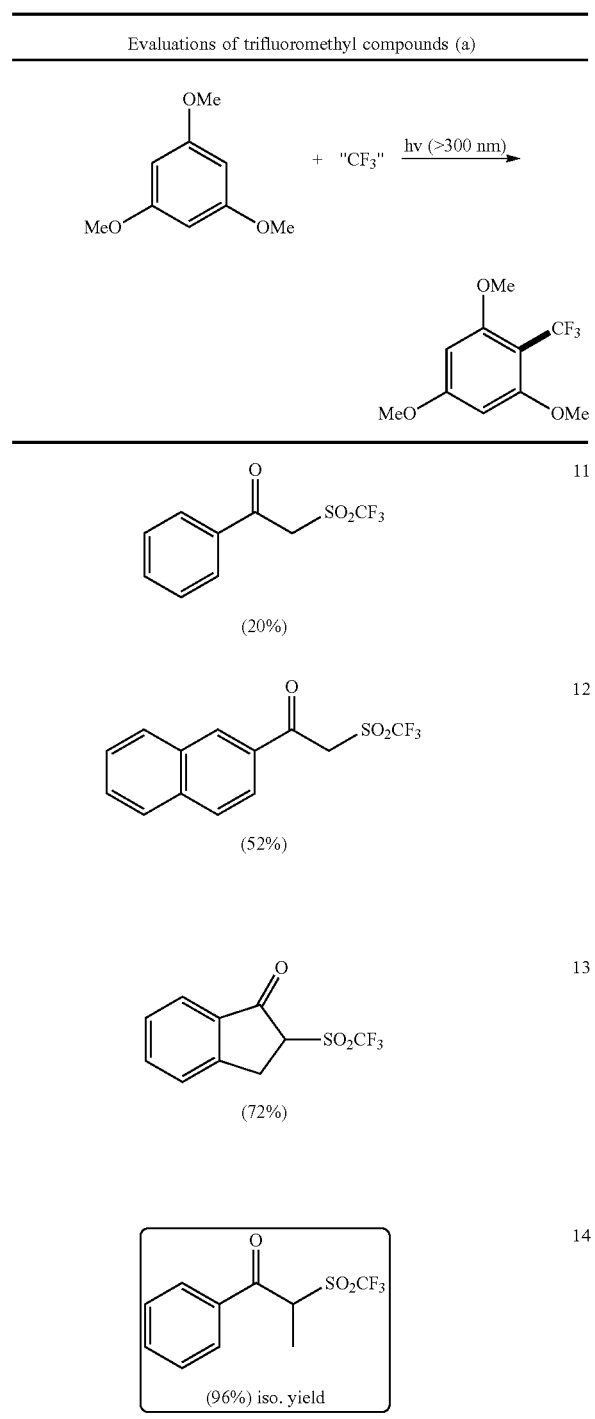

[a]All the reactions were conducted with 1,3,5-trimethoxybenzene (0.05 mmol), CF$_3$ source (0.075 mmol) in 0.25 mL CH$_3$CN under argon for 12 h at rt (ca. 25° C.) and the reaction yields were quantified by $^1$H-NMR via mesitylene as the internal standard except 14.

Applicant is also providing a representative number of reaction with one of the trifluoromethylation reagent in accordance with the invention towards both aromatic and heteroaromatic rings (Table 2). It was observed that both aromatic and heteroaromatic rings provide the desired reaction product. The broad functional group compatibility also illustrates the usefulness of this reagent in the context of trifluoromethylation. Table 2. Arenes for the

TABLE 2

Arenes for the trifluoromethylation

R—⟨C₆H₅⟩ + Ph-C(=O)-CH(CH₃)-SO₂CF₃ →(hv (>300 nm), CH₃CN, r.t.)→ R—⟨C₆H₄⟩-CF₃

1 equiv + 14 (1.5-3 equiv)

15: 2,4,6-trimethoxy-(CF₃)-benzene (96%, [b] 12 h)

16: 2,3,4,6-tetramethoxy-(CF₃)-benzene (76%, [c] 12 h)

17: methyl 3,4,5-trimethoxy-2-(CF₃)-benzoate (73%, [c] 24 h)

18: 2-acetyl-3,4,6-trimethoxy-(CF₃)-benzene (68%, [c] 12 h)

19: 2,5-dimethoxy-(CF₃)-benzene (70%, [c] 12 h)

TABLE 2-continued

Arenes for the trifluoromethylation

20: 2,4,6-trimethyl-(CF₃)-benzene (71%, [d,e] 12 h)

21: 2,6-di-tert-butyl-4-(CF₃)-phenol (78%, [c] 12 h)

22: 2,5-dimethyl-(CF₃)-benzene (61%, [c,e] 12 h)

23: 1-phenyl-2-(CF₃)-pyrrole (71%, [b] 8 h)

24: 2-phenyl-3-(CF₃)-1H-indole (91%, [b] 3 h; 78%, 1.35 g, 24 h)

25: 3-methyl-2-phenyl-1H-indole (75%, [b] 2 h)

TABLE 2-continued
Arenes for the trifluoromethylation
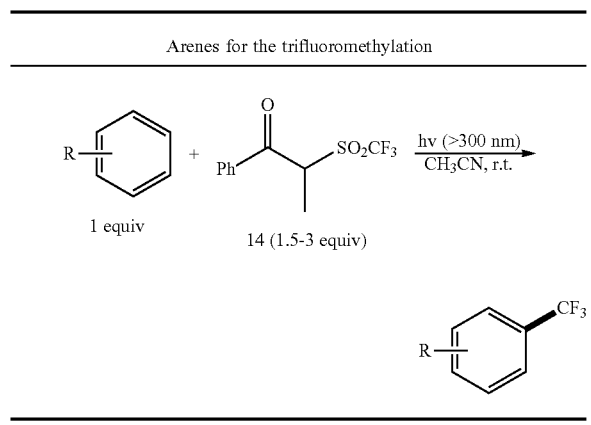
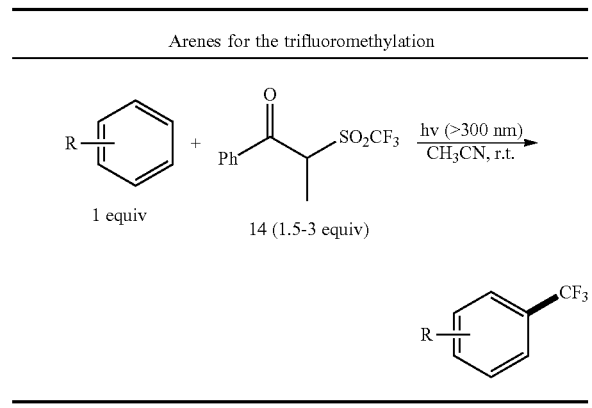
| | |
|---|---|
| 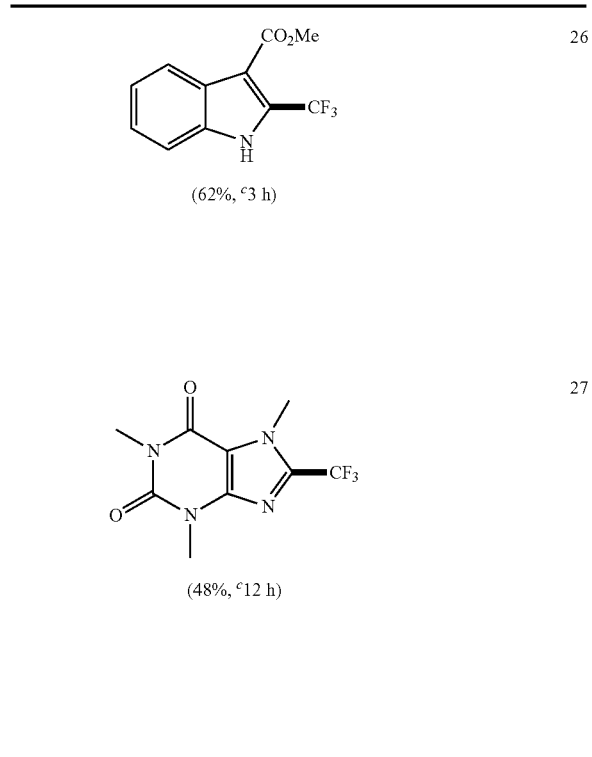 (62%, $^c$3 h) 26 | 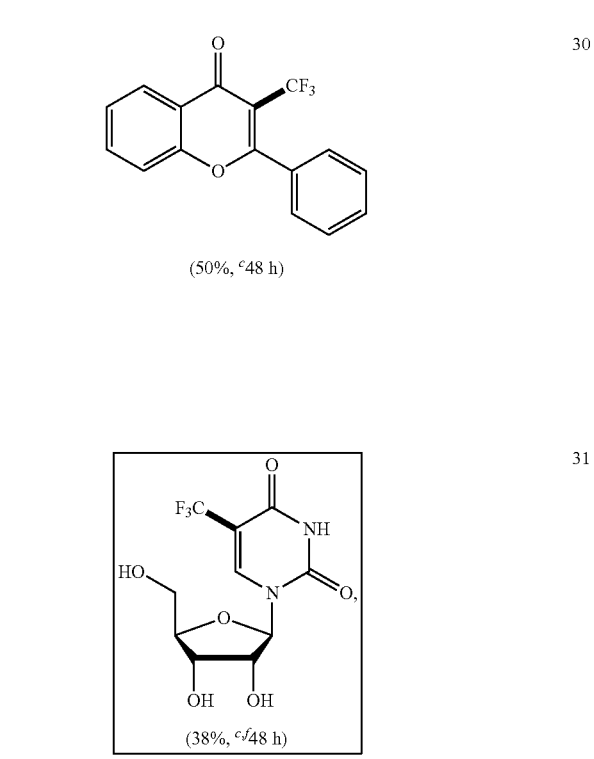 (50%, $^c$48 h) 30 |
| (48%, $^c$12 h) 27 | |
| 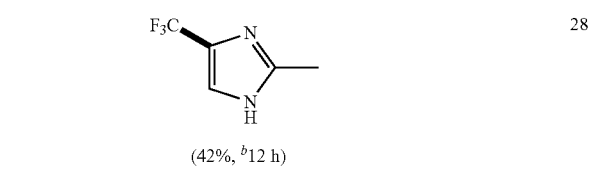 (42%, $^b$12 h) 28 | 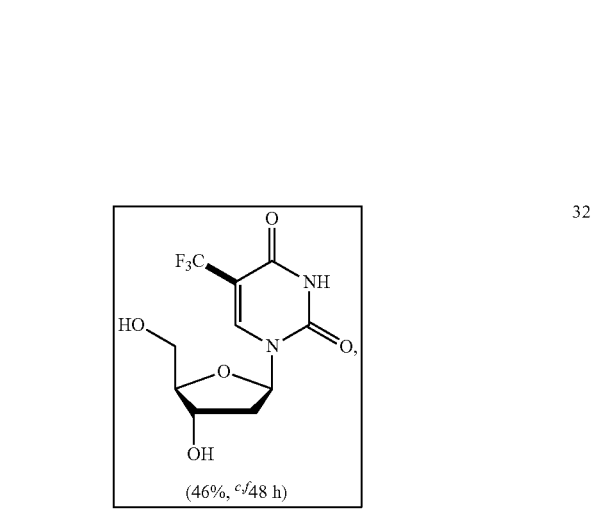 (38%, $^{c,f}$48 h) 31 |
| 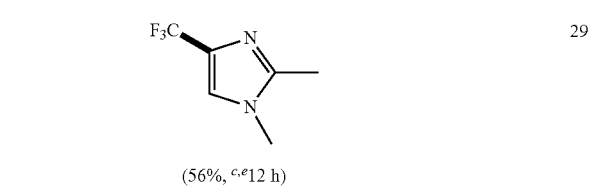 (56%, $^{c,e}$12 h) 29 | (46%, $^{c,f}$48 h) 32 |

TABLE 2-continued

Arenes for the trifluoromethylation

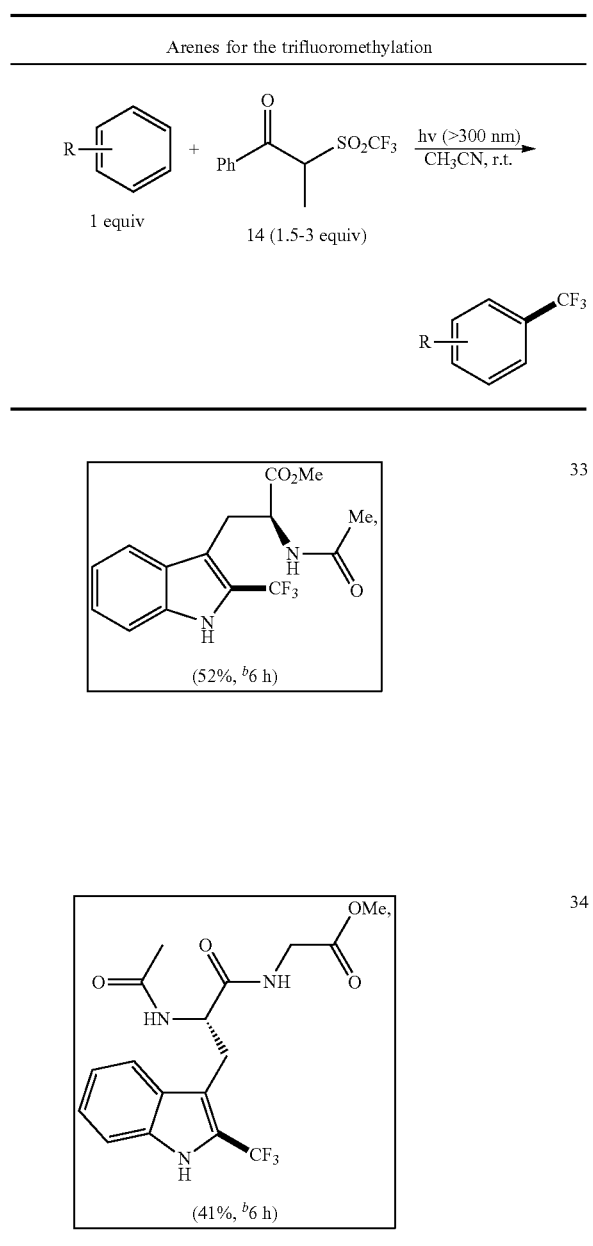

$^a$All the reactions were conducted with arene (0.1 mmol), CH$_3$CN (0.5 mL), 300 watts Xenon lamp under argon with specified amount of CF$_3$ source 14 at rt (ca. 25° C.) and the yields are isolated ones.

$^b$1.5 equiv 14.

$^c$3.0 equiv 14.

$^d$2.0 equiv 14.

$^e$Yields were quantified by GC-MS due to volatility of products.

$^f$0.1 mL H$_2$O was added into 0.5 mL CH$_3$CN.

To further demonstrate the flexibility and robustness of the reagent according to the invention, Applicant also demonstrated that a simple household compact fluorescence lamp (CFL) could be employed as the light source to promote the reactions (Table 3). The lower yields driven by CFL compared to Xenon lamp can be attributed to the lower conversion of the starting material however prolonging the reaction time can enhance the conversion rate and consequently the reaction yields.

TABLE 3

CFL as light source to promote the trifluoromethylation$^a$

| Entry | Product (yield) |
|---|---|
| 15 | 2,4,6-trimethoxy-CF$_3$ benzene (73%, 78%$^b$) |
| 19 | 2,4-dimethoxy-CF$_3$ benzene (42%, 44%$^b$) |
| 20 | mesityl-CF$_3$ (36%$^d$, 39%$^c$) |
| 23 | 1-phenyl-2-CF$_3$-pyrrole (57%, 65%$^b$) |
| 24 | 2-phenyl-3-CF$_3$-indole (80%, 90%$^b$) |
| 25 | 3-methyl-2-CF$_3$-indole (40%, 46%$^b$) |

TABLE 3-continued

CFL as light source to promote the trifluoromethylation[a]

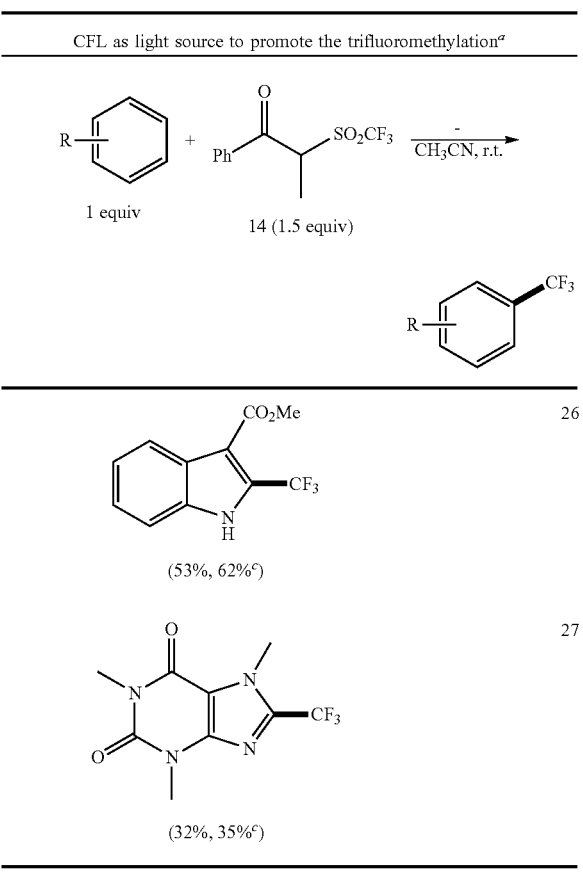

(53%, 62%[c])

(32%, 35%[c])

[a]All the reactions were conducted with arene (0.1 mmol), 14 (0.15 mmol), CH$_3$CN (0.5 mL), 45 watts CFL under argon for 48 h and the yields are isolated ones, which are followed by the conversion in the parenthesis.
[b]The conversion was calibrated by $^1$H-NMR.
[c]The conversion was calibrated by GC/MS.
[d]This yield was determined by GC/MS due to its volatility.

Applicant has next demonstrated the alkylation or aromatic and heteroaromatic rings. The nucleophilic alkyl radical tends to react with the electron-deficient heteroaromatics in acidic conditions. Therefore, the reaction between 2-phenyl quinoline 35 and isopropyl radical source 36 were used (Table 4). CH$_3$CN was employed with 1 equiv of TFA at room temperature. Changing the reaction solvent and the temperature allowed for changing the yield.

TABLE 4 alkylation of 2-phenylquinoline

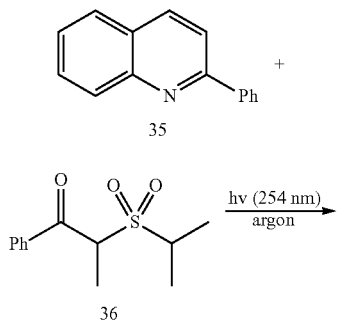

TABLE 4-continued

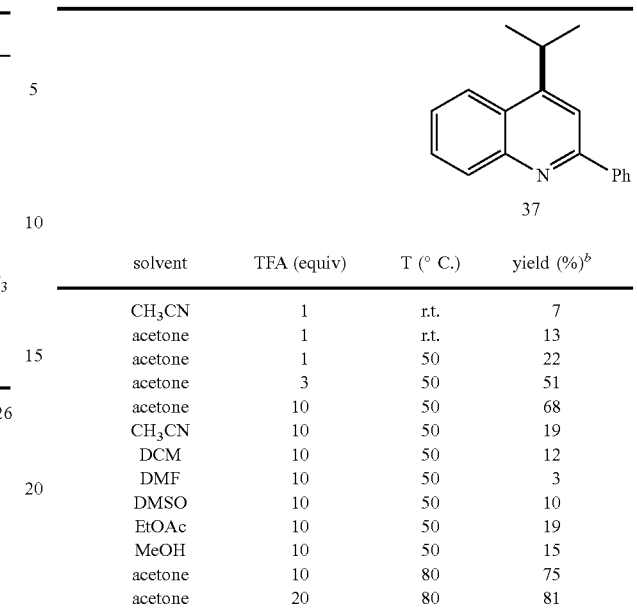

| solvent | TFA (equiv) | T (° C.) | yield (%)[b] |
|---|---|---|---|
| CH$_3$CN | 1 | r.t. | 7 |
| acetone | 1 | r.t. | 13 |
| acetone | 1 | 50 | 22 |
| acetone | 3 | 50 | 51 |
| acetone | 10 | 50 | 68 |
| CH$_3$CN | 10 | 50 | 19 |
| DCM | 10 | 50 | 12 |
| DMF | 10 | 50 | 3 |
| DMSO | 10 | 50 | 10 |
| EtOAc | 10 | 50 | 19 |
| MeOH | 10 | 50 | 15 |
| acetone | 10 | 80 | 75 |
| acetone | 20 | 80 | 81 |

[a]All the reactions were conducted with 0.1 mmol 35, 0.15 mmol 36 in 0.5 mL solvent with a 300 Watts mercury lamp under argon for 10 h.
[b]The yield was determined by GC/MS.

Applicant has next demonstrated the scope of the invention by expanding the nature of the heteroaromatic rings (Table 5). Different substituents can be present on the ring.

TABLE 5

Heteroarenes for the alkylation[a]

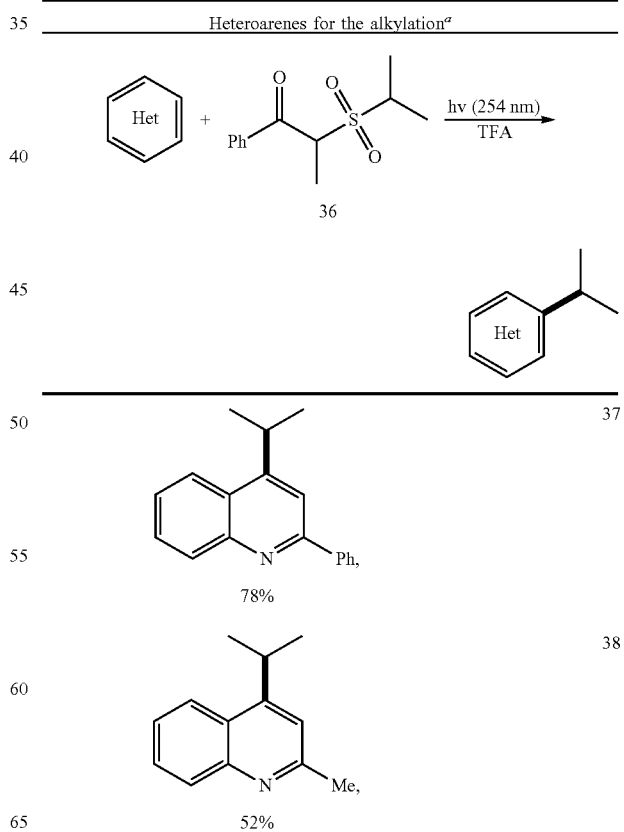

TABLE 5-continued
Heteroarenes for the alkylation[a]
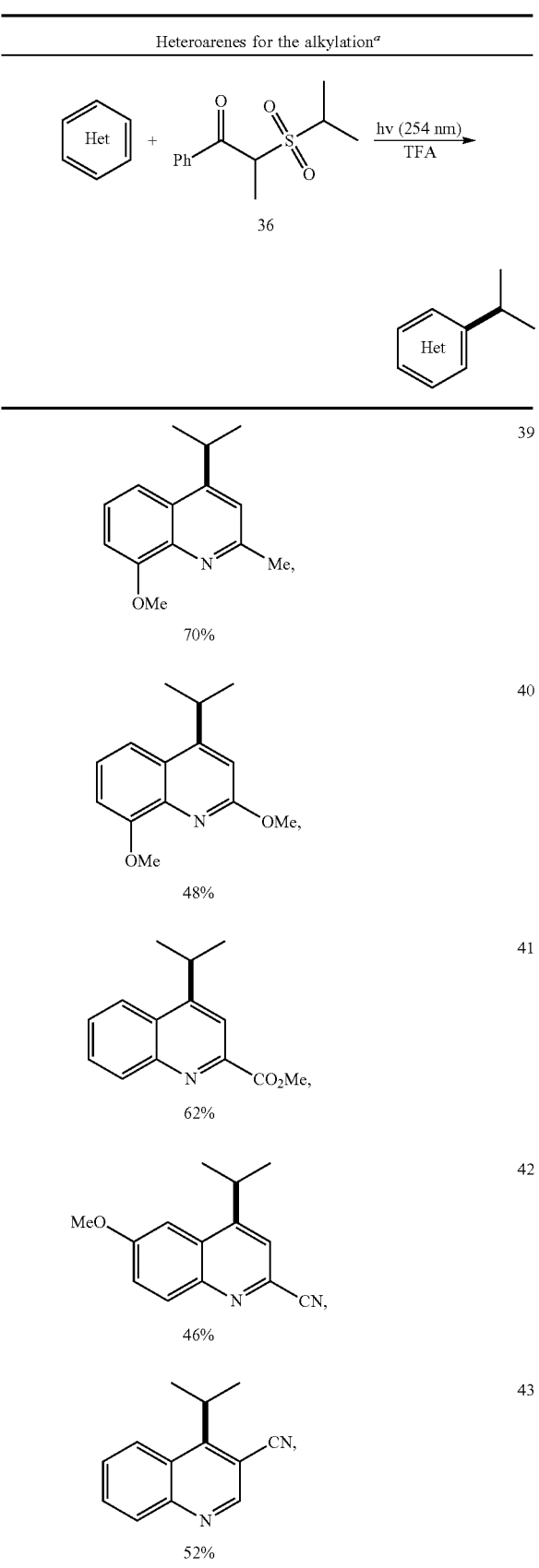
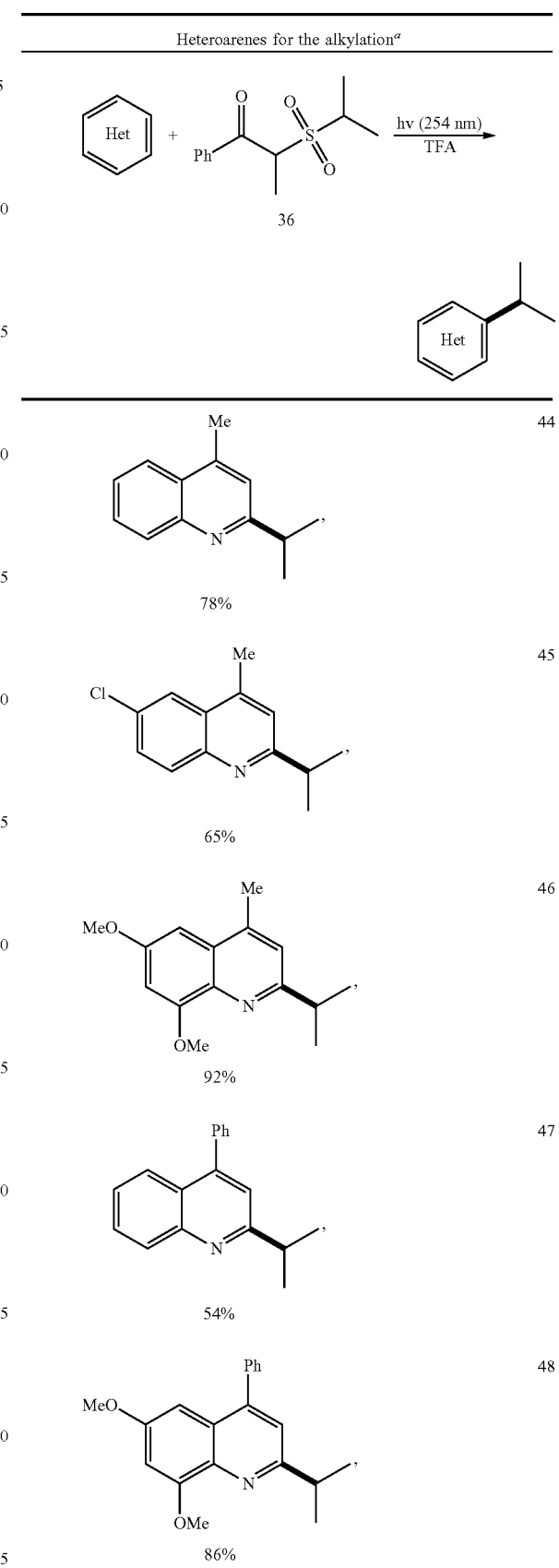

TABLE 5-continued

Heteroarenes for the alkylation[a]

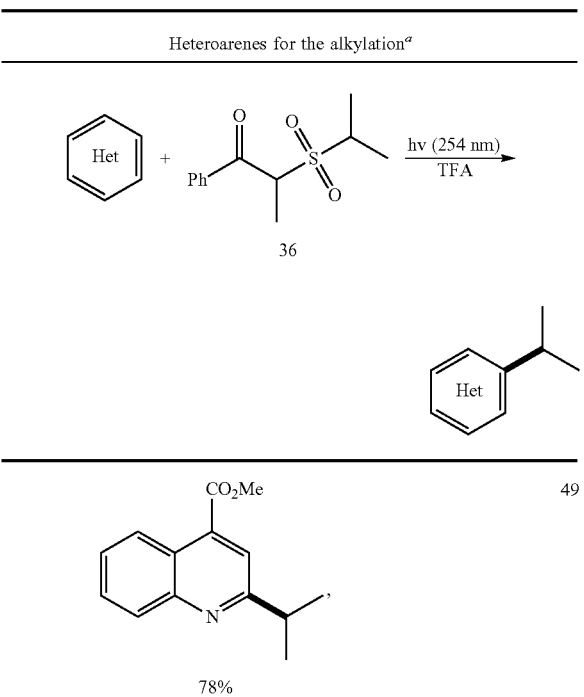
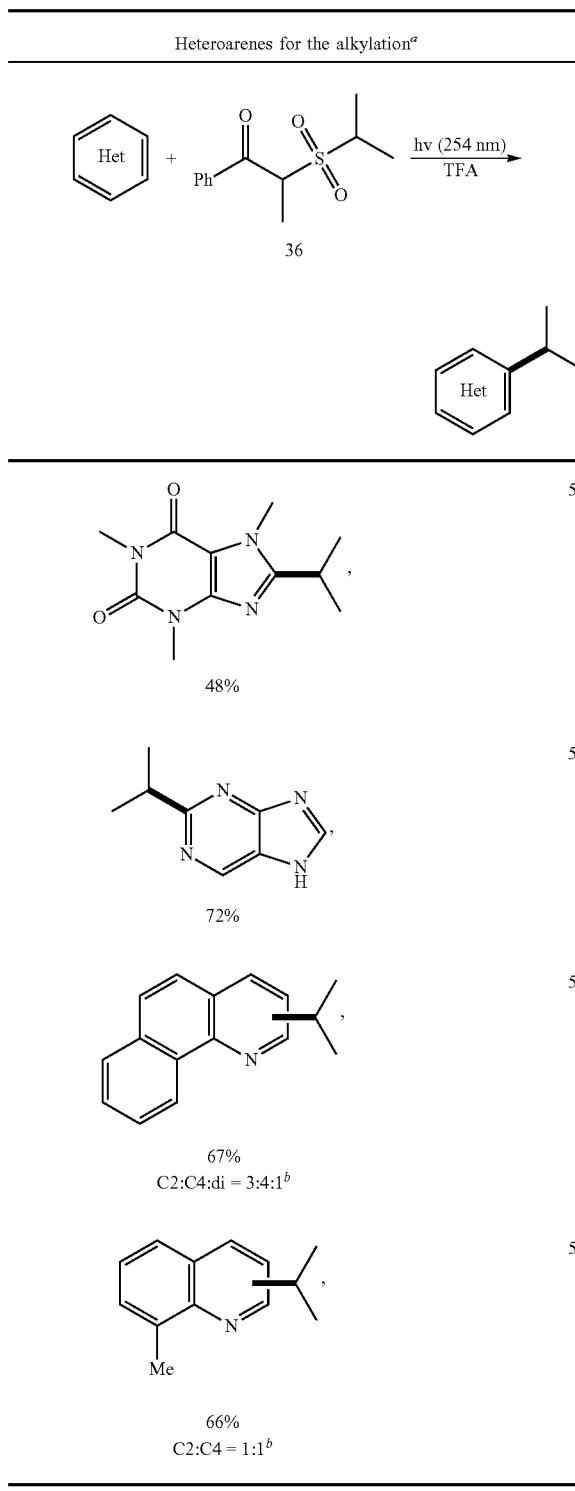

[a]All the reactions were conducted with 0.1 mmol heteroarene, 0.12 mmol 36 in 0.5 mL acetone with a 300 watts mercury lamp under argon for 10 h.
[b]isolated yield and the ratio of different isomers for 56 and 57 was determined by GC/MS.

Other alkyl substituents were also evaluated (Table 6). It was found that primary (58-60, 68), secondary (61, 65-67) and tertiary alkyl groups (62) can all alkylate the heteroarenes in good yields (32%-72%) even with only 1.5 equiv of alkylation reagents.

TABLE 6
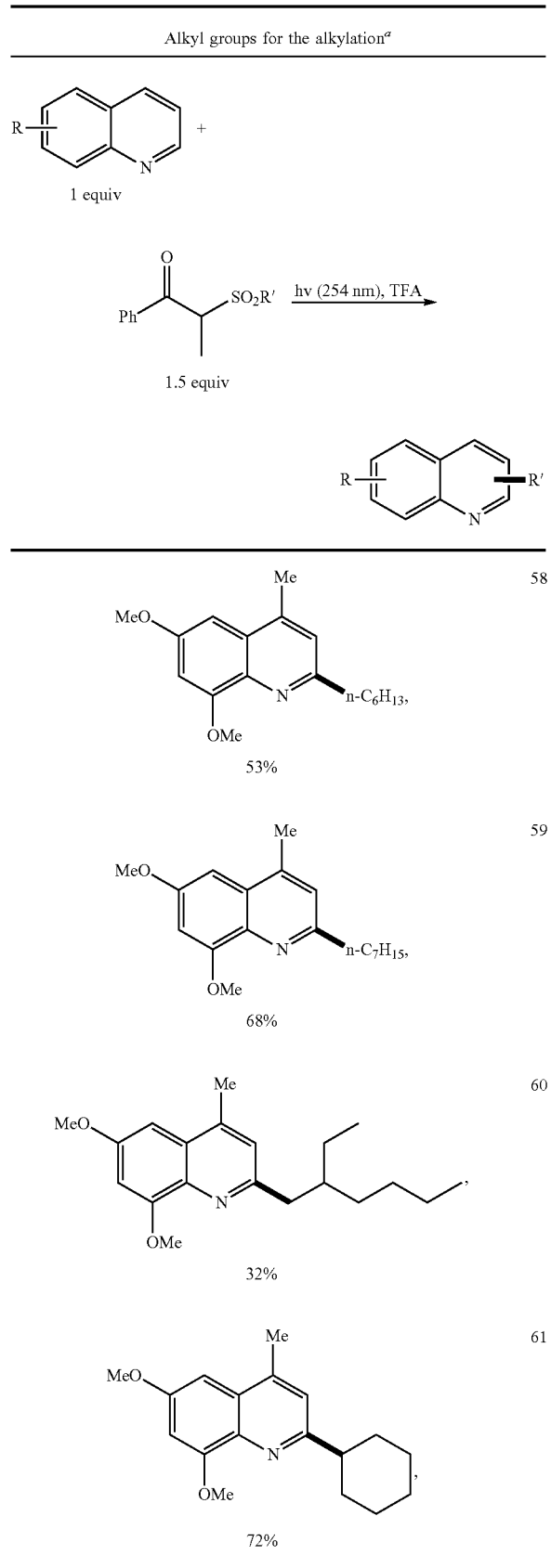
TABLE 6-continued
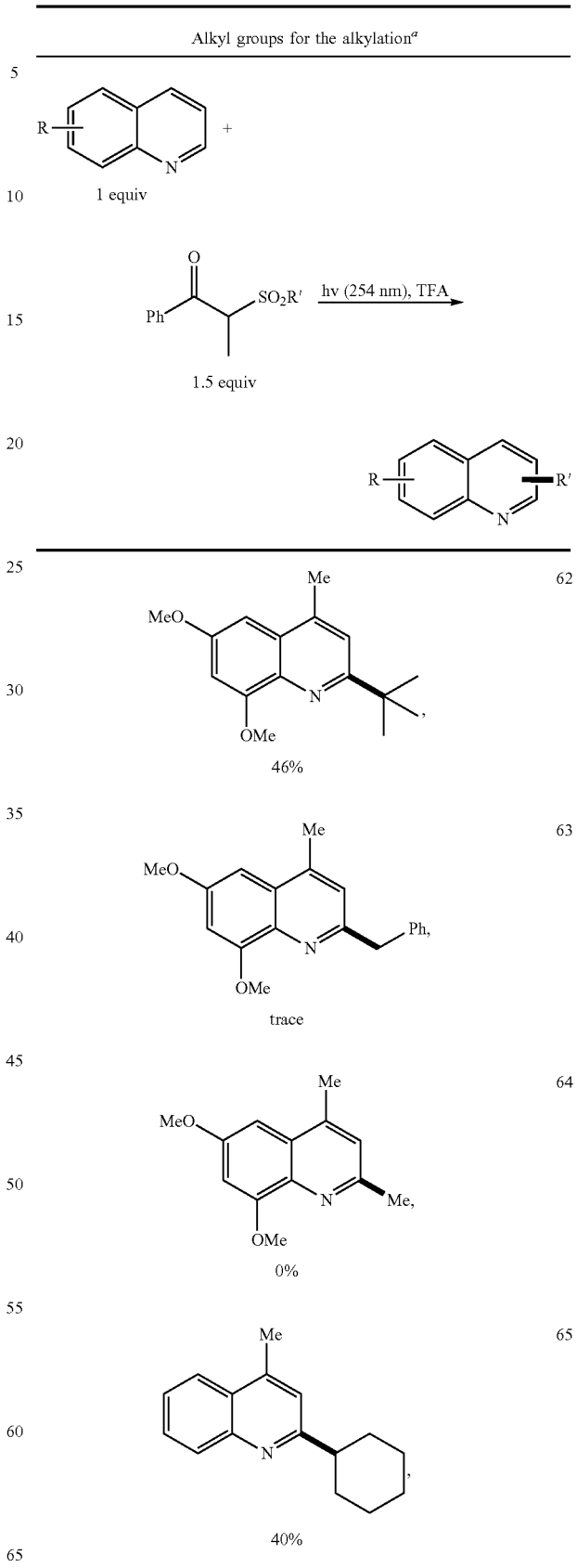

TABLE 6-continued

Alkyl groups for the alkylation[a]

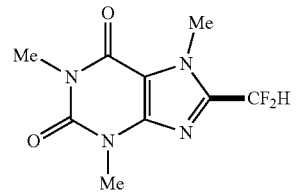
50%

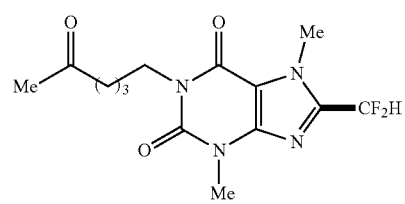
52%

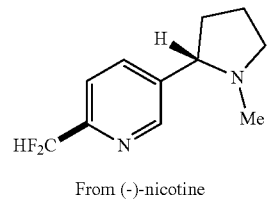
38%

[a]All the reactions were conducted with 0.1 mmol heteroarene, 0.15 mmol alkylation reagents in 0.5 mL acetone with a 300 watts' mercury lamp under argon for 10 h and the yields are isolated ones.

Yet next, the applicants demonstrated the scope of difluoromethylation reactions. Both 5 an d6-membered heteroarenes can give the difrluomethylation products upon photo irridation.

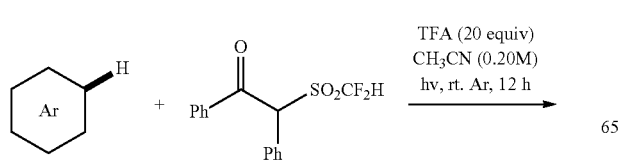

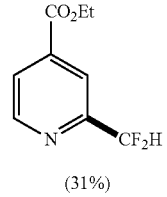

1b

From caffeine
(84%)

2b

From pentoxifylline
(52%)

3b

From (-)-nicotine
(31%)

4b (87%, $C_2$:$C_2$ + $C_4$ = 2:1)

5b (48%)

6b (31%)

-continued

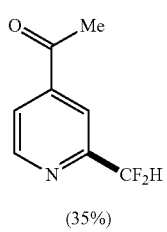

(35%)

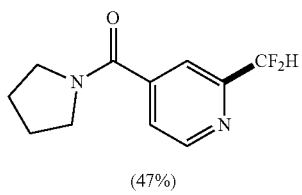

(47%)

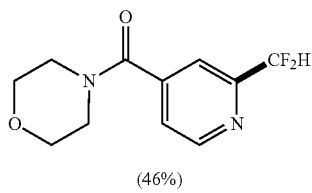

(46%)

Characterization Data of Compounds

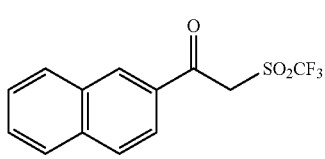

1-Phenyl-2-((trifluoromethyl)sulfonyl)ethan-1-one (11)

Eluent: hexane/ethyl acetate (10:1). Yield: 76%. Yellow oil. $^1$H NMR (500 MHz, CDCl$_3$) δ 7.95 (dd, J=8.4, 1.2 Hz, 2H), 7.71-7.65 (m, 1H), 7.53 (t, J=7.9 Hz, 2H), 4.88 (s, 2H). $^{13}$C NMR (126 MHz, CDCl$_3$) δ 184.8, 135.3, 135.1, 129.3, 129.2, 119.3 (q, J=327.6 Hz), 56.9. $^{19}$F NMR (471 MHz, CDCl$_3$) δ −77.2.

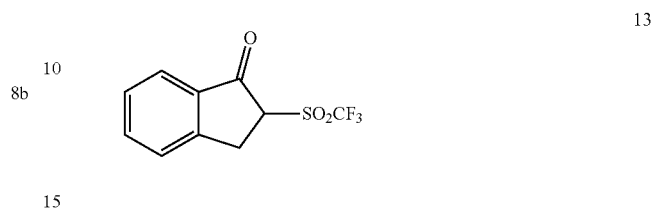

1-(Naphthalen-2-yl)-2-((trifluoromethyl)sulfonyl)ethan-1-one (12)

Eluent: hexane/ethyl acetate (10:1). Yield: 68%. White solid. $^1$H NMR (500 MHz, CDCl$_3$) δ 8.48 (d, J=1.3 Hz, 1H), 8.02 (dd, J=8.7, 1.9 Hz, 2H), 7.97 (d, J=8.7 Hz, 1H), 7.92 (d, J=7.9 Hz, 1H), 7.69 (ddd, J=8.2, 6.9, 1.3 Hz, 1H), 7.63 (ddd, J=8.1, 7.0, 1.2 Hz, 1H), 4.97 (s, 2H). $^{13}$C NMR (126 MHz, CDCl$_3$) δ 184.4, 136.5, 132.6, 132.4, 132.3, 130.1, 130.0, 129.4, 128.1, 127.6, 123.7, 119.4 (q, J=327.6 Hz), 57.1. $^{19}$F NMR (471 MHz, CDCl$_3$) δ −76.9. HRMS (ESI) calcd for C$_{13}$H$_9$F$_3$NaO$_3$S [M+Na]$^+$: 325.0106, found 325.0117.

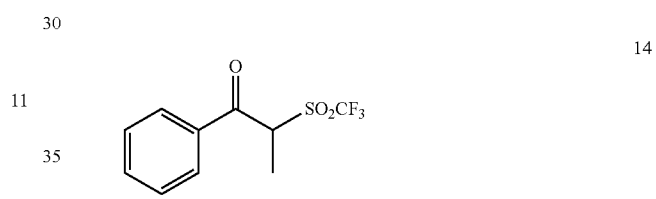

2-((Trifluoromethyl)sulfonyl)-2,3-dihydro-1H-inden-1-one (13)

Eluent: Hexane/ethyl acetate (10:1). Yield: 82%. Colorless oil. $^1$H NMR (500 MHz, CDCl$_3$) δ 7.84 (d, J=7.3 Hz, 1H), 7.75-7.69 (m, 1H), 7.56 (d, J=7.8 Hz, 1H), 7.52-7.46 (m, 1H), 4.53-4.51 (m, 1H), 3.84-3.80 (m, 1H), 3.73-3.59 (m, 1H). $^{13}$C NMR (126 MHz, CDCl$_3$) δ 190.8, 151.2, 136.8, 135.0, 129.0, 126.7, 125.5, 119.7 (q, J=330.1 Hz), 64.4, 27.8. $^{19}$F NMR (471 MHz, CDCl$_3$) δ −74.5. HRMS (ESI) calcd for C10H7F3NaO3S [M+H]$^+$: 286.9960, found 286.9968.

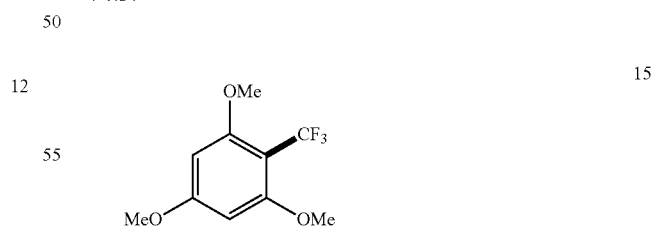

1-Phenyl-2-((trifluoromethyl)sulfonyl)propan-1-one (14)

Eluent: Hexane/ethyl acetate (10:1). Yield: 82%. Colorless oil. 1H NMR (500 MHz, CDCl$_3$) δ 7.98 (dd, J=8.4, 1.2 Hz, 2H), 7.74-7.64 (m, 1H), 7.55 (t, J=7.9 Hz, 2H), 5.33 (q, J=7.0 Hz, 1H), 1.84 (d, J=7.0 Hz, 3H). $^{13}$C NMR (126 MHz, CDCl$_3$) δ 189.1, 135.1, 135.0, 129.3, 129.2, 119.8 (q, J=330.1 Hz), 61.3, 13.0. $^{19}$F NMR (471 MHz, CDCl$_3$) δ −74.3.

1,3,5-Trimethoxy-2-(trifluoromethyl)benzene (15)

Eluent: Hexane/ethyl acetate (10:1). Yield: 96%. White solid. $^1$H NMR (500 MHz, CDCl$_3$) δ 6.13 (s, 2H), 3.84 (s, 6H), 3.83 (s, 3H). $^{13}$C NMR (126 MHz, CDCl$_3$) δ 163.6, 160.5, 124.5 (q, J=276.8 Hz), 100.5 (q, J=30.2 Hz), 91.4, 56.4, 55.5. $^{19}$F NMR (471 MHz, CDCl$_3$) δ −54.1.

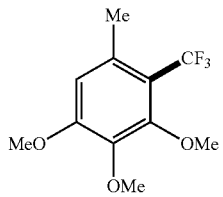

1,2,3-Trimethoxy-5-methyl-4-(trifluoromethyl)benzene (16)

Eluent: Hexane/ethyl acetate (10:1). Yield: 76%. Colorless oil. $^1$H NMR (500 MHz, CDCl$_3$) δ 6.49 (s, 1H), 3.91 (s, 3H), 3.88 (s, 3H), 3.85 (s, 3H), 2.42 (q, J=3.4 Hz, 3H). $^{13}$C NMR (126 MHz, CDCl$_3$) δ 155.3, 153.5 (q, J=1.9 Hz), 141.1, 133.2 (q, J=1.8 Hz), 125.0 (q, J=274.7 Hz), 115.6 (q, J=29.0 Hz), 110.9, 61.9, 60.9, 56.1, 21.70 (q, J=4.2 Hz). $^{19}$F NMR (471 MHz, CDCl$_3$) δ −54.3.

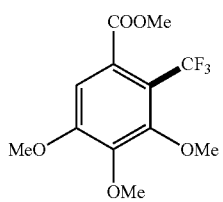

Methyl 3,4,5-trimethoxy-2-(trifluoromethyl)benzoate (17)

Eluent: Hexane/ethyl acetate (10:1). Yield: 73%. Colorless liquid. $^1$H NMR (500 MHz, CDCl$_3$) δ 6.75 (s, 1H), 3.95 (s, 3H), 3.91 (s, 3H), 3.89 (s, 6H). $^{13}$C NMR (126 MHz, CDCl$_3$) δ 168.6, 156.0, 153.1, 144.3, 128.6 (q, J=2.9 Hz), 123.2 (q, J=273.8 Hz), 114.7 (q, J=31.0 Hz), 107.0, 62.0, 61.1, 56.4, 53.2. $^{19}$F NMR (471 MHz, CDCl$_3$) δ −56.9.

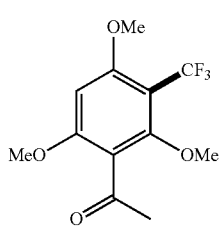

1-(2,4,6-Trimethoxy-3-(trifluoromethyl)phenyl)ethan-1-one (18)

Eluent: Hexane/ethyl acetate (10:1). Yield: 68%. White solid. $^1$H NMR (500 MHz, CDCl$_3$) δ 6.30 (s, 1H), 3.91 (s, 3H), 3.86 (s, 3H), 3.76 (s, 3H), 2.48 (s, 3H). $^{13}$C NMR (126 MHz, CDCl$_3$) δ 201.2, 161.0, 159.9, 157.8, 123.7 (q, J=274.3 Hz), 119.9, 105.5 (q, J=30.2 Hz), 92.2, 64.8, 56.6, 56.0, 32.6. $^{19}$F NMR (471 MHz, CDCl$_3$) δ −55.8.

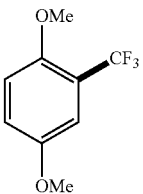

1,4-Dimethoxy-2-(trifluoromethyl)benzene (19)

Eluent: Hexane/ethyl acetate (10:1). Yield: 70%. Colorless liquid. $^1$H NMR (500 MHz, CDCl$_3$) δ 7.12 (d, J=3.1 Hz, 1H), 7.02 (dd, J=9.0, 3.1 Hz, 1H), 6.94 (d, J=9.0 Hz, 1H), 3.86 (s, 3H), 3.80 (s, 3H). $^{13}$C NMR (126 MHz, CDCl$_3$) δ 153.1, 151.7 (q, J=1.7 Hz), 123.6 (q, J=273.4 Hz), 119.6 (q, J=30.5 Hz), 118.3, 113.8, 113.0 (q, J=5.2 Hz), 56.8, 56.1. $^{19}$F NMR (471 MHz, CDCl$_3$) δ −62.4.

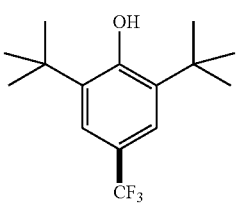

2,6-Di-tert-butyl-4-(trifluoromethyl)phenol (21)

Eluent: Hexane/ethyl acetate (5:1). Yield: 78%. White solid. $^1$H NMR (500 MHz, CDCl$_3$) δ 7.41 (s, 2H), 5.55 (br, 1H), 1.46 (s, 18H). $^{13}$C NMR (126 MHz, CDCl$_3$) δ 156.6, 136.4, 125.1 (q, J=272.2 Hz), 122.4 (q, J=3.8 Hz), 121.6 (q, J=31.5 Hz), 34.6, 30.2. $^{19}$F NMR (471 MHz, CDCl$_3$) δ −61.2.

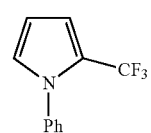

1-Phenyl-2-(trifluoromethyl)-1H-pyrrole (23)

Eluent: Hexane/ethyl acetate (10:1). Yield: 71%. Colorless oil. $^1$H NMR (500 MHz, CDCl$_3$) δ 7.49-7.42 (m, 3H), 7.39-7.37 (m, 2H), 6.93-6.86 (m, 1H), 6.77-6.71 (m, 1H), 6.32-6.25 (m, 1H). $^{13}$C NMR (126 MHz, CDCl$_3$) δ 139.3, 129.1, 128.6, 127.4 (q, J=1.9 Hz), 126.6 (q, J=1.0 Hz), 122.4, (q, J=38.3 Hz), 121.4 (q, J=267.1 Hz), 112.8 (q, J=3.4 Hz), 108.4. $^{19}$F NMR (471 MHz, CDCl$_3$) δ −55.9.

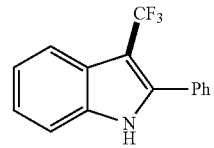

2-Phenyl-3-(trifluoromethyl)-1H-indole (24)

Eluent: Hexane/ethyl acetate (8:1). Yield: 91%. Yellow solid. ¹H NMR (500 MHz, CDCl₃) δ 8.34 (br, 1H), 7.83 (d, J=7.9 Hz, 1H), 7.62-7.60 (m, 2H), 7.53-7.45 (m, 3H), 7.43 (d, J=7.9 Hz, 1H), 7.33-7.24 (m, 2H). ¹³C NMR (126 MHz, CDCl₃) δ 138.7 (q, J=3.8 Hz), 135.0, 131.2, 129.5, 129.2, 128.8, 125.7 (q, J=1.7 Hz), 124.9 (q, J=267.1 Hz), 123.6, 121.8, 120.2, 111.2, 103.7 (q, J=35.7 Hz). ¹⁹F NMR (471 MHz, CDCl₃) δ −52.9.

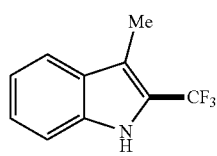

25

3-Methyl-2-(trifluoromethyl)-1H-indole (25)

Eluent: Hexane/ethyl acetate (5:1). Yield: 75%. White solid. ¹H NMR (500 MHz, CDCl₃) δ 8.16 (br, 1H), 7.64 (d, J=8.0 Hz, 1H), 7.39 (d, J=8.3 Hz, 1H), 7.35-7.30 (m, 1H), 7.22-7.17 (m, 1H), 2.45 (q, J=1.8 Hz, 3H). ¹³C NMR (126 MHz, CDCl₃) δ 135.3, 128.2, 124.9, 122.2 (q, J=268.4 Hz), 121.6 (q, J=36.5 Hz), 120.5, 120.2, 114.2 (q, J=3.0 Hz), 111.7, 8.5. ¹⁹F NMR (471 MHz, CDCl₃) δ −58.7.

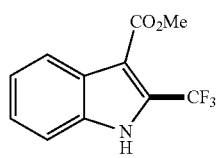

26

Methyl 2-(trifluoromethyl)-1H-indole-3-carboxylate (26)

Eluent: Hexane/ethyl acetate (8:1). Yield: 62%. Colorless oil. ¹H NMR (500 MHz, CDCl₃) δ 9.03 (br, 1H), 8.26 (d, J=8.1 Hz, 1H), 7.48 (d, J=8.2 Hz, 1H), 7.40 (t, J=7.5 Hz, 1H), 7.35 (t, J=7.6 Hz, 1H), 3.98 (s, 3H). ¹³C NMR (126 MHz, CDCl₃) δ 163.6, 133.9, 129.0 (q, J=39.0 Hz), 126.6, 125.7, 123.4, 123.0, 120.5 (q, J=270.9 Hz), 112.0, 108.5, 51.8. ¹⁹F NMR (471 MHz, CDCl₃) δ −59.9.

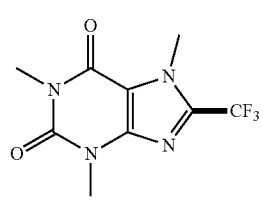

27

Caffeine-CF₃[10] (27)

Eluent: DCE/Methanol (10:1). Yield: 48%. White solid. ¹H NMR (500 MHz, CDCl₃) δ 4.15 (s, 3H), 3.59 (s, 3H), 3.41 (s, 3H). ¹³C NMR (126 MHz, CDCl₃) δ 155.6, 151.5, 146.7, 139.1 (q, J=40.3 Hz), 118.3 (q, J=271.7 Hz), 109.8, 33.3 (q, J=1.9 Hz), 30.0, 28.3. ¹⁹F NMR (471 MHz, CDCl₃) δ −62.4.

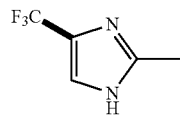

28

2-Methyl-4-(trifluoromethyl)-1H-imidazole (28)

Eluent: DCE/Methanol (10:1). Yield: 42%. White solid. ¹H NMR (500 MHz, (CD₃)₂CO) δ 7.50 (s, 1H), 2.36 (s, 3H). ¹³C NMR (126 MHz, (CD₃)₂CO) δ 147.0, 131.3 (q, J=37.8 Hz), 123.4 (q, J=265.9 Hz), 117.4, 13.8. ¹⁹F NMR (471 MHz, (CD₃)₂CO) δ −62.9.

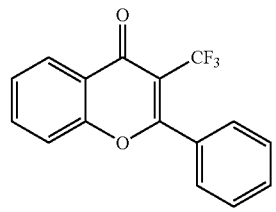

30

2-Phenyl-3-(trifluoromethyl)-4-chromenone (CF3-flavone, 30)

Eluent: Hexane/ethyl acetate (8:1). Yield: 50%. Yellow oil. ¹H NMR (500 MHz, CDCl₃) δ 8.28 (dd, J=8.4, 1.6 Hz, 1H), 7.77-7.71 (m, 1H), 7.62-7.57 (m, 3H), 7.55-7.51 (m, 2H), 7.50-7.47 (m, 2H). ¹³C NMR (126 MHz, CDCl₃) δ 174.5, 167.2, 155.6, 134.9, 132.6, 131.5, 129.0, 128.7 (q, J=3.2 Hz), 128.5, 126.3, 123.5, 122.8 (q, J=273.4 Hz), 118.1, 113.3 (q, J=29.0 Hz). ¹⁹F NMR (471 MHz, CDCl₃) δ −56.2.

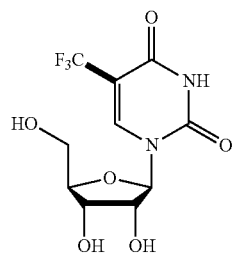

31

5-Trifluoromethyluridine (31)

Eluent: DCE/Methanol (10:1). Yield: 38%. White solid. ¹H NMR (500 MHz, d₄-MeOH) δ 8.90 (s, 1H), 5.89 (d, J=2.7 Hz, 1H), 4.21-4.17 (m, 2H), 4.06 (dt, J=5.0, 2.3 Hz, 1H), 3.92 (dd, J=12.1, 2.5 Hz, 1H), 3.76 (dd, J=12.1, 2.1 Hz, 1H). ¹³C NMR (126 MHz, d₄-MeOH) δ 161.2, 151.5, 143.9 (q, J=2.8 Hz), 123.9 (q, J=268.9 Hz), 105.4 (q, J=32.9 Hz), 91.6, 86.2, 76.4, 70.5, 61.2. ¹⁹F NMR (471 MHz, d₄-MeOH) δ −64.5.

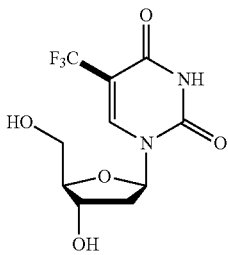

Trifluridine (32)

Eluent: DCE/Methanol (10:1). Yield: 46%. White solid. $^1$H NMR (500 MHz, d$_4$-MeOH) δ 8.79 (s, 1H), 6.24 (t, J=6.2 Hz, 1H), 4.41 (dt, J=6.0, 4.0 Hz, 1H), 3.97 (dd, J=6.2, 3.0 Hz, 1H), 3.84 (dd, J=11.9, 2.8 Hz, 1H), 3.74 (dd, J=11.9, 2.8 Hz, 1H), 2.37 (ddd, J=13.6, 6.2, 4.3 Hz, 1H), 2.31-2.23 (m, 1H). $^{13}$C NMR (126 MHz, d$_4$-MeOH) δ 161.2, 151.3, 143.8 (q, J=6.3 Hz), 123.9 (q, J=269.6 Hz), 105.3 (q, J=32.8 Hz), 89.3, 87.5, 71.7, 62.1, 42.1. $^{19}$F NMR (471 MHz, d$_4$-MeOH) δ -64.5.

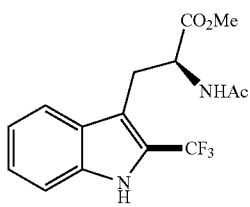

Methyl (S)-2-acetamido-3-(2-(trifluoromethyl)-1H-indol-3-yl)propanoate (33)

Eluent: DCE/Methanol (30:1). Yield: 52%. Yellow oil. $^1$H NMR (500 MHz, CDCl$_3$) δ 8.61 (s, 1H), 7.71 (d, J=8.1 Hz, 1H), 7.38 (d, J=8.3 Hz, 1H), 7.32 (t, J=7.6 Hz, 1H), 7.20 (ddd, J=8.0, 7.0, 1.0 Hz, 1H), 6.05 (d, J=7.8 Hz, 1H), 4.96 (dd, J=14.3, 6.2 Hz, 1H), 3.67 (s, 3H), 3.45-3.36 (m, 2H), 1.94 (s, 3H). $^{13}$C NMR (101 MHz, CDCl$_3$) δ 172.2, 169.9, 135.4, 127.5, 125.3, 122.7 (q, J=36.7 Hz), 122.0 (q, J=269.7 Hz), 121.1, 120.3, 112.4 (q, J=2.5 Hz), 112.0, 52.7, 52.6, 27.2, 23.2. $^{19}$F NMR (377 MHz, CDCl$_3$) δ -57.93. HRMS (ESI) calcd for C$_{15}$H$_{16}$N$_2$O$_3$F$_3$[M+H]$^+$: 329.1107, found 329.1101.

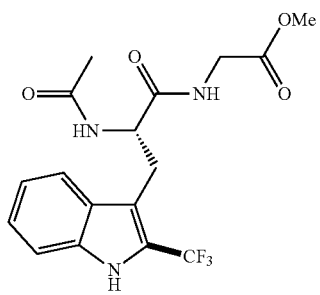

Methyl (S)-(2-acetamido-3-(2-(trifluoromethyl)-1H-indol-3-yl)propanoyl)glycinate (34)

Eluent: DCE/Methanol (30:1). Yield: 41%. White solid. $^1$H NMR (400 MHz, d$_6$-DMSO) δ 11.90 (s, 1H), 8.32 (t, J=5.8 Hz, 1H), 8.09 (d, J=9.0 Hz, 1H), 7.80 (d, J=8.1 Hz, 1H), 7.40 (d, J=8.2 Hz, 1H), 7.26 (t, J=7.3 Hz, 1H), 7.14-7.07 (m, 1H), 4.59 (td, J=8.6, 5.5 Hz, 1H), 3.81-3.74 (m, 2H), 3.60 (s, 3H), 3.30-3.28 (m, 1H), 3.02 (dd, J=15.0, 8.3 Hz, 1H), 1.71 (s, 3H). $^{13}$C NMR (101 MHz, d$_6$-DMSO) δ 171.3, 170.0, 168.9, 135.6, 127.0, 124.1, 122.2 (q, J=270.7 Hz), 121.4 (q, J=35.6 Hz), 120.4, 119.7, 113.0 (q, J=3.0 Hz), 112.1, 53.4, 51.7, 40.7, 26.9, 22.5. $^{19}$F NMR (377 MHz, d$_6$-DMSO) δ -56.2. HRMS (ESI) calcd for C$_{17}$H$_{18}$N$_3$O$_4$F$_3$Na [M+Na]$^+$: 408.1141, found 408.1130.

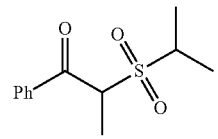

2-(Isopropylsulfonyl)-1-phenylpropan-1-one (36)

Eluent: Hexane/ethyl acetate (5:1). Yield: 80%. White solid. 1H NMR (500 MHz, CDCl$_3$) δ 8.02 (d, J=8.3 Hz, 2H), 7.64 (t, J=7.4 Hz, 1H), 7.52 (t, J=7.8 Hz, 2H), 5.04 (q, J=7.1 Hz, 1H), 3.51-3.39 (m, 1H), 1.75 (dd, J=7.1, 1.1 Hz, 3H), 1.44 (d, J=6.9 Hz, 3H), 1.31 (d, J=6.9 Hz, 3H). $^{13}$C NMR (126 MHz, CDCl$_3$) δ 193.6, 135.9, 134.4, 129.2, 129.1, 62.4, 52.5, 15.9, 15.9, 13.2. HRMS (ESI) calcd for C$_{12}$H$_{15}$O$_3$S [M+H]$^+$: 239.0747, found 239.0740.

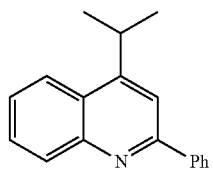

4-Isopropyl-2-phenylquinoline (37)

Eluent: Hexane/ethyl acetate (5:1). Yield: 78%. Yellow oil. $^1$H NMR (500 MHz, CDCl$_3$) δ 8.20 (dd, J=8.4, 0.7 Hz, 1H), 8.15 (d, J=7.1 Hz, 2H), 8.11 (d, J=8.4 Hz, 1H), 7.78 (s, 1H), 7.71 (ddd, J=8.3, 6.8, 1.3 Hz, 1H), 7.56-7.48 (m, 3H), 7.49-7.44 (m, 1H), 3.87-3.73 (m, 1H), 1.47 (d, J=6.9 Hz, 6H). $^{13}$C NMR (126 MHz, CDCl$_3$) δ 157.5, 155.0, 148.7, 140.4, 130.8, 129.3, 129.2, 128.9, 127.8, 126.1, 126.0, 123.1, 115.1, 28.7, 23.2.

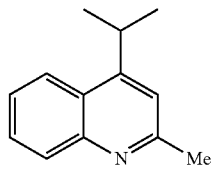

4-Isopropyl-2-methylquinoline (38)

Eluent: Hexane/ethyl acetate (3:1). Yield: 52%. Yellow oil. $^1$H NMR (500 MHz, CDCl$_3$) δ 8.09-8.01 (m, 2H), 7.65 (ddd, J=8.3, 6.9, 1.3 Hz, 1H), 7.49 (ddd, J=8.2, 6.9, 1.2 Hz, 1H), 7.19 (s, 1H), 3.74-3.68 (m, 1H), 2.73 (s, 3H), 1.39 (d, J=6.9 Hz, 6H). $^{13}$C NMR (126 MHz, CDCl$_3$) δ 159.0, 154.4, 148.3, 129.7, 128.9, 125.5, 125.3, 123.0, 117.9, 28.4, 25.7, 23.1.

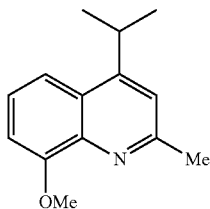

4-Isopropyl-8-methoxy-2-methylquinoline (39)

Eluent: Hexane/ethyl acetate (5:1). Yield: 70%. Yellow oil. $^1$H NMR (500 MHz, CDCl$_3$) δ 7.61 (d, J=8.4 Hz, 1H), 7.43-7.38 (m, 1H), 7.22 (s, 1H), 7.02 (d, J=7.6 Hz, 1H), 4.07 (s, 3H), 3.69-3.64 (m, 1H), 2.77 (s, 3H), 1.38 (d, J=6.9 Hz, 6H). $^{13}$C NMR (126 MHz, CDCl$_3$) δ 158.0, 155.5, 154.3, 140.1, 126.4, 125.3, 118.4, 115.0, 107.1, 56.1, 28.7, 26.1, 23.1. HRMS (ESI) calcd for C$_{14}$H$_{18}$ON [M+H]$^+$: 216.1388, found 216.1383.

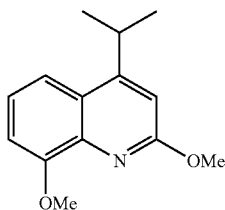

4-Isopropyl-2,8-dimethoxyquinoline (40)

Eluent: Hexane/ethyl acetate (6:1). Yield: 48%.
Colorless oil. Mixture with starting material. $^1$H NMR (500 MHz, CDCl$_3$) δ 7.56 (d, J=8.2 Hz, 1H), 7.34-7.28 (m, 1H), 7.05-7.03 (m, 1H), 6.85 (s, 1H), 4.12 (s, 3H), 4.05 (s, 3H), 3.62-3.57 (m, 1H), 1.36 (d, J=6.8 Hz, 6H). $^{13}$C NMR (126 MHz, CDCl$_3$) δ 162.2, 157.3, 154.8, 138.5, 125.3, 123.6, 115.5, 109.0, 108.7, 56.5, 53.3, 28.8, 22.9. HRMS (ESI) calcd for C$_{14}$H$_{17}$NNaO$_2$ [M+Na]$^+$: 254.1159, found 254.1151.

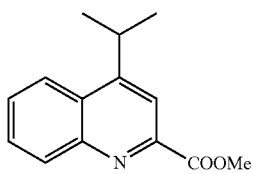

Methyl 4-isopropylquinoline-2-carboxylate (41)

Eluent: Hexane/ethyl acetate (6:1). Yield: 62%. Yellow oil. $^1$H NMR (500 MHz, CDCl$_3$) δ 8.32 (dd, J=8.5, 0.7 Hz, 1H), 8.15 (d, J=8.5 Hz, 1H), 8.13 (s, 1H), 7.76 (ddd, J=8.3, 6.8, 1.3 Hz, 1H), 7.66 (ddd, J=8.3, 6.8, 1.3 Hz, 1H), 4.09 (s, 3H), 3.79 (hept, J=6.8 Hz, 1H), 1.45 (d, J=6.9 Hz, 6H). $^{13}$C NMR (126 MHz, CDCl$_3$) δ 166.5, 156.2, 148.0, 147.9, 131.8, 129.8, 128.4, 128.2, 123.2, 117.1, 53.3, 28.8, 23.0. HRMS (ESI) calcd for C$_{14}$H$_{15}$NNaO$_2$ [M+Na]$^+$: 252.1000, found 252.0995.

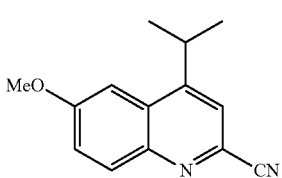

4-Isopropyl-6-methoxyquinoline-2-carbonitrile (42)

Eluent: Hexane/ethyl acetate (5:1). Yield: 46%. Yellow solid. $^1$H NMR (500 MHz, CDCl$_3$) δ 8.07 (d, J=9.3 Hz, 1H), 7.56 (s, 1H), 7.46 (dd, J=9.3, 2.7 Hz, 1H), 7.30 (d, J=2.7 Hz, 1H), 3.99 (s, 3H), 3.70-3.60 (m, 1H), 1.42 (d, J=6.9 Hz, 6H). $^{13}$C NMR (126 MHz, CDCl$_3$) δ 159.9, 154.6, 144.7, 132.7, 131.2, 129.0, 123.4, 120.0, 118.4, 101.2, 55.8, 28.9, 22.6. HRMS (ESI) calcd for C$_{14}$H$_{14}$N$_2$NaO [M+Na]$^+$: 249.1011, found 249.0998.

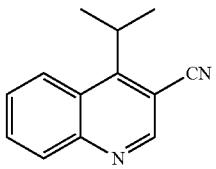

4-Isopropylquinoline-3-carbonitrile (43)

Eluent: Hexane/ethyl acetate (3:1). Yield: 52%. White solid. $^1$H NMR (500 MHz, CDCl$_3$) δ 8.95 (s, 1H), 8.30 (d, J=8.6 Hz, 1H), 8.17 (dd, J=8.4, 0.7 Hz, 1H), 7.85 (ddd, J=8.3, 6.9, 1.2 Hz, 1H), 7.67 (ddd, J=8.3, 6.9, 1.2 Hz, 1H), 4.08-4.02 (m, 1H), 1.65 (d, J=7.2 Hz, 6H). $^{13}$C NMR (126 MHz, CDCl$_3$) δ 160.4, 151.5, 149.3, 132.0, 131.1, 127.9, 125.5, 124.4, 117.9, 105.0, 29.8, 21.7. HRMS (APCI) calcd for C$_{13}$H$_{13}$N$_2$ [M+H]$^+$: 197.10765, found 197.10732.

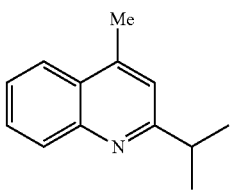

2-Isopropyl-4-methylquinoline (44)

Eluent: Hexane/ethyl acetate (5:1). Yield: 78%. Colorless oil. $^1$H NMR (500 MHz, CDCl$_3$) δ 8.04 (d, J=8.4 Hz, 1H), 7.95 (dd, J=8.3, 0.9 Hz, 1H), 7.67 (ddd, J=8.3, 6.9, 1.4 Hz, 1H), 7.50 (ddd, J=8.2, 6.9, 1.2 Hz, 1H), 7.18 (s, 1H), 3.24-3.18 (m, 1H), 2.69 (s, 3H), 1.39 (d, J=7.0 Hz, 6H). $^{13}$C NMR (126 MHz, CDCl$_3$) δ 167.5, 147.7, 144.4, 129.7, 129.1, 127.2, 125.5, 123.7, 119.9, 37.4, 22.7, 19.0.

2-Isopropyl-4-phenylquinoline (47)

Eluent: Hexane/ethyl acetate (5:1). Yield: 54%. Yellow oil. $^1$H NMR (500 MHz, CDCl$_3$) δ 8.15 (d, J=8.4 Hz, 1H), 7.88 (d, J=8.4 Hz, 1H), 7.71 (ddd, J=8.3, 6.9, 1.3 Hz, 1H), 7.59-7.50 (m, 5H), 7.46 (ddd, J=8.2, 6.9, 1.1 Hz, 1H), 7.30 (s, 1H), 3.35-3.30 (m, 1H), 1.46 (d, J=7.0 Hz, 6H). $^{13}$C NMR (126 MHz, CDCl$_3$) δ 167.3, 148.9, 148.4, 138.7, 129.7, 129.5, 129.3, 128.6, 128.4, 125.8, 125.7, 125.6, 119.5, 37.5, 22.7. HRMS (APCI) calcd for C$_{18}$H$_{18}$N [M+H]$^+$: 248.14359, found 248.14338.

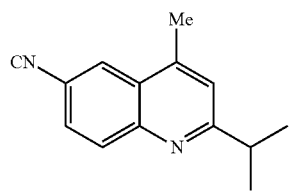

45

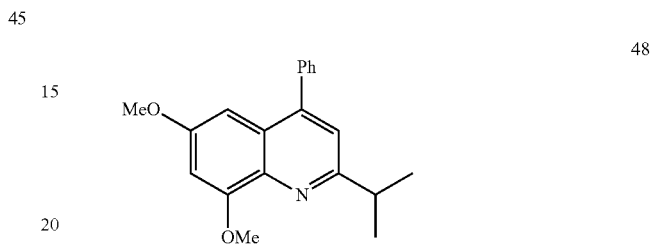

48

6-Chloro-2-isopropyl-4-methylquinoline (45)

Eluent: Hexane/ethyl acetate (5:1). Yield: 65%. Yellow oil. $^1$H NMR (500 MHz, CDCl$_3$) δ 7.97 (d, J=8.9 Hz, 1H), 7.91 (d, J=2.3 Hz, 1H), 7.59 (dd, J=8.9, 2.3 Hz, 1H), 7.18 (s, 1H), 3.26-3.14 (m, 1H), 2.65 (s, 3H), 1.37 (d, J=7.0 Hz, 6H). $^{13}$C NMR (126 MHz, CDCl$_3$) δ 167.8, 146.2, 143.7, 131.3, 131.3, 129.8, 127.9, 122.8, 120.8, 37.3, 22.6, 18.9. HRMS (ESI) calcd for C$_{13}$H$_{15}$NCl [M+H]$^+$: 220.08917, found 220.08875.

2-Isopropyl-6,8-dimethoxy-4-phenylquinoline (48)

Eluent: Hexane/ethyl acetate (5:1). Yield: 86%. White solid. $^1$H NMR (500 MHz, CDCl$_3$) δ 8.14 (d, J=7.1 Hz, 2H), 7.78 (s, 1H), 7.49 (t, J=7.6 Hz, 2H), 7.41 (t, J=7.3 Hz, 1H), 6.91 (d, J=2.4 Hz, 1H), 6.74 (d, J=2.4 Hz, 1H), 4.06 (s, 3H), 3.96 (s, 3H), 3.68-3.61 (m, 1H), 1.46 (d, J=6.8 Hz, 6H). $^{13}$C NMR (126 MHz, CDCl$_3$) δ 157.9, 157.2, 153.8, 153.2, 140.4, 137.1, 128.65, 128.64, 127.44, 127.43, 115.7, 100.7, 93.0, 56.2, 55.5, 29.0, 22.8. HRMS (ESI) calcd for C$_{20}$H$_{22}$NO$_2$ [M+H]$^+$: 308.1654, found 308.1645.

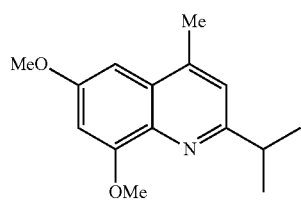

46

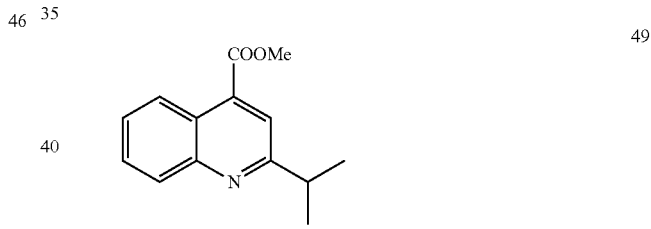

49

2-Isopropyl-6,8-dimethoxy-4-methylquinoline (46)

Eluent: Hexane/ethyl acetate (5:1). Yield: 92%. Yellow oil. $^1$H NMR (500 MHz, CDCl$_3$) δ 7.18 (s, 1H), 6.72 (d, J=2.5 Hz, 1H), 6.70 (d, J=2.4 Hz, 1H), 4.03 (s, 3H), 3.92 (s, 3H), 3.32-3.27 (m, 1H), 2.61 (s, 3H), 1.35 (d, J=7.0 Hz, 6H). $^{13}$C NMR (126 MHz, CDCl$_3$) δ 164.1, 157.5, 156.6, 143.1, 135.8, 128.6, 120.2, 100.7, 93.6, 56.4, 55.5, 37.5, 23.1, 19.7. HRMS (ESI) calcd for C$_{15}$H$_{20}$NO$_2$ [M+H]$^+$: 246.1495, found 246.1489.

Methyl 2-isopropylquinoline-4-carboxylate (49)

Eluent: Hexane/ethyl acetate (5:1). Yield: 78%. Yellow oil. $^1$H NMR (500 MHz, CDCl$_3$) δ 8.67 (d, J=8.6 Hz, 1H), 8.10 (dd, J=8.4, 0.5 Hz, 1H), 7.84 (s, 1H), 7.73 (ddd, J=8.3, 6.9, 1.3 Hz, 1H), 7.58 (ddd, J=8.3, 6.9, 1.2 Hz, 1H), 4.05 (s, 3H), 3.30 (hept, J=6.8 Hz, 1H), 1.42 (d, J=6.9 Hz, 6H). $^{13}$C NMR (126 MHz, CDCl$_3$) δ 167.2, 167.2, 148.8, 135.5, 129.7, 129.7, 127.3, 125.5, 123.8, 120.9, 52.8, 37.4, 22.5. HRMS (ESI) calcd for C$_{14}$H$_{16}$NO$_2$ [M+H]$^+$: 230.1179, found 230.1176.

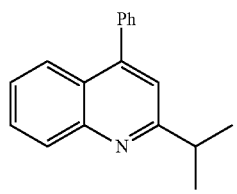

47

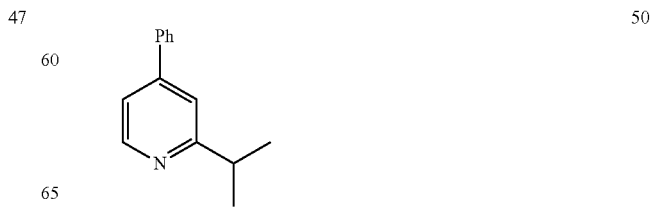

50

2-Isopropyl-4-phenylpyridine (50)

Eluent: Hexane/ethyl acetate (6:1). Yield: 43%. Pale yellow oil. $^1$H NMR (500 MHz, CDCl$_3$) δ 8.59 (d, J=5.1 Hz, 1H), 7.67-7.61 (m, 2H), 7.48 (t, J=7.3 Hz, 2H), 7.45-7.41 (m, 1H), 7.38 (s, 1H), 7.32 (dd, J=5.1, 1.8 Hz, 1H), 3.16-3.11 (m, 1H), 1.36 (d, J=6.9 Hz, 6H). $^{13}$C NMR (126 MHz, CDCl$_3$) δ 168.0, 149.6, 149.0, 138.9, 129.2, 129.0, 127.2, 119.4, 118.9, 36.6, 22.8.

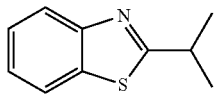

2-Isopropylbenzo[d]thiazole (51)

Eluent: Hexane/ethyl acetate (5:1). Yield: 84%. Pale yellow oil. $^1$H NMR (500 MHz, CDCl$_3$) δ 7.98 (d, J=8.1 Hz, 1H), 7.85 (d, J=8.0 Hz, 1H), 7.48-7.41 (m, 1H), 7.38-7.31 (m, 1H), 3.46-3.40 (m, 1H), 1.49 (d, J=6.9 Hz, 6H). $^{13}$C NMR (126 MHz, CDCl$_3$) δ 178.7, 153.3, 134.8, 126.0, 124.7, 122.7, 121.7, 34.2, 23.1.

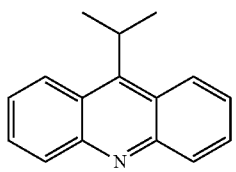

9-Isopropylacridine (52)

Eluent: Hexane/ethyl acetate (10:1). Yield: 66%. Pale yellow oil. $^1$H NMR (500 MHz, CDCl$_3$) δ 8.44 (d, J=8.9 Hz, 2H), 8.23 (dd, J=8.7, 0.5 Hz, 2H), 7.74 (ddd, J=8.7, 6.5, 1.2 Hz, 2H), 7.52 (ddd, J=8.8, 6.5, 1.2 Hz, 2H), 4.57-4.51 (m, 1H), 1.77 (d, J=7.3 Hz, 6H). $^{13}$C NMR (126 MHz, CDCl$_3$) δ 152.1, 149.2, 130.9, 129.9, 129.5, 125.1, 124.7, 28.6, 23.0.

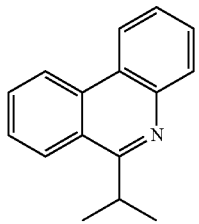

6-Isopropylphenanthridine (53)

Eluent: Hexane/ethyl acetate (10:1). Yield: 86%. Yellow oil. $^1$H NMR (500 MHz, CDCl$_3$) δ 8.66 (d, J=8.3 Hz, 1H), 8.54 (dd, J=8.2, 1.3 Hz, 1H), 8.33 (d, J=8.3 Hz, 1H), 8.15 (dd, J=8.2, 1.0 Hz, 1H), 7.82 (ddd, J=8.3, 7.0, 1.2 Hz, 1H), 7.72-7.68 (m, 2H), 7.61 (ddd, J=8.3, 7.0, 1.3 Hz, 1H), 4.01 (hept, J=6.8 Hz, 1H), 1.53 (d, J=6.8 Hz, 6H). $^{13}$C NMR (126 MHz, CDCl$_3$) δ 166.0, 143.9, 133.2, 130.1, 130.1, 128.5, 127.2, 126.3, 125.8, 124.9, 123.6, 122.7, 121.9, 31.6, 22.1.

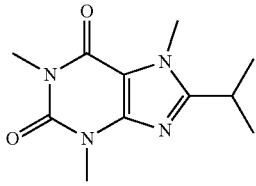

8-Isopropyl-1,3,9-trimethyl-1H-purine-2,6(3H,9H)-dione (54)

Eluent: DCE/Methanol (10:1). Yield: 48%. White solid. $^1$H NMR (500 MHz, CDCl$_3$) δ 3.92 (s, 3H), 3.57 (s, 3H), 3.39 (s, 3H), 3.09-3.04 (m, 1H), 1.34 (d, J=6.9 Hz, 6H). $^{13}$C NMR (126 MHz, CDCl$_3$) δ 158.9, 155.6, 151.9, 148.2, 107.3, 31.5, 29.9, 28.0, 26.3, 21.0.

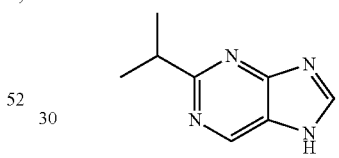

2-Isopropyl-7H-purine (55)

Eluent: DCE/Methanol (10:1). Yield: 72%. Yellow oil. $^1$H NMR (500 MHz, d$_4$-MeOH) δ 8.80 (s, 1H), 8.45 (s, 1H), 3.76-3.65 (m, 1H), 1.43 (d, J=6.9 Hz, 6H). $^{13}$C NMR (126 MHz, d$_4$-MeOH) δ 165.8, 155.7, 153.1, 146.5, 129.4, 33.0, 21.4. HRMS (APCI) calcd for C$_8$H$_{11}$N$_4$ [M+H]$^+$: 163.0977, found 163.0978.

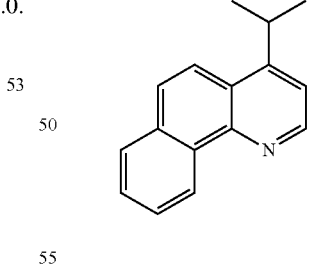

4-Isopropylbenzo[h]quinolone (56)

Eluent: Hexane/ethyl acetate (10:1). Yield: 67%. Colorless oil. $^1$H NMR (500 MHz, CDCl$_3$) δ 9.33 (d, J=8.1 Hz, 1H), 8.95 (d, J=4.7 Hz, 1H), 8.02 (d, J=9.2 Hz, 1H), 7.91 (d, J=7.4 Hz, 1H), 7.84 (d, J=9.2 Hz, 1H), 7.75-7.66 (m, 2H), 7.45 (d, J=4.7 Hz, 1H), 3.82 (dt, J=13.7, 6.8 Hz, 1H), 1.44 (d, J=6.9 Hz, 6H). $^{13}$C NMR (126 MHz, CDCl$_3$) δ 154.3, 148.9, 146.6, 133.2, 132.3, 128.1, 127.7, 127.4, 127.1, 125.0, 124.7, 120.8, 118.0, 28.7, 23.2. HRMS (ESI) calcd for C$_{16}$H$_{16}$N [M+H]$^+$: 222.1278, found 222.1277.

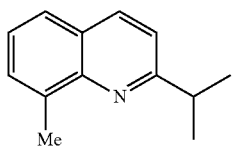

2-Isopropyl-8-methylquinoline (57)

Eluent: Hexane/ethyl acetate (10:1). Yield: 66%. Yellow oil. $^1$H NMR (500 MHz, CDCl$_3$) δ 8.03 (d, J=8.5 Hz, 1H), 7.60 (d, J=8.1 Hz, 1H), 7.51 (d, J=6.9 Hz, 1H), 7.35 (t, J=7.5 Hz, 1H), 7.31 (d, J=8.5 Hz, 1H), 3.31-3.18 (m, 1H), 2.81 (s, 3H), 1.40 (d, J=6.9 Hz, 6H). $^{13}$C NMR (126 MHz, CDCl$_3$) δ 166.2, 146.8, 137.2, 136.3, 129.3, 126.8, 125.5, 125.3, 119.4, 37.3, 22.7, 17.9.

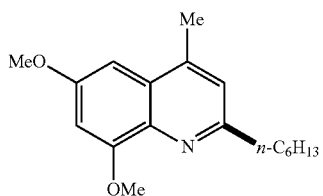

2-Hexyl-6,8-dimethoxy-4-methylquinoline (58)

Eluent: Hexane/ethyl acetate (10:1). Yield: 53%. Yellow solid. $^1$H NMR (500 MHz, CDCl$_3$) δ 7.15 (s, 1H), 6.73 (d, J=2.5 Hz, 1H), 6.70 (d, J=2.5 Hz, 1H), 4.03 (s, 3H), 3.93 (s, 3H), 2.93 (d, J=7.5 Hz, 2H), 2.60 (s, 3H), 1.81-1.74 (m, 2H), 1.45-1.39 (m, 2H), 1.35-1.30 (m, 4H), 0.91-0.86 (m, 3H). $^{13}$C NMR (126 MHz, CDCl$_3$) δ 159.3, 157.4, 156.5, 142.8, 136.2, 128.3, 123.0, 100.6, 93.6, 56.3, 55.6, 39.4, 32.0, 30.4, 29.6, 22.7, 19.6, 14.2. HRMS (ESI) calcd for C$_{18}$H$_{26}$NO$_2$ [M+H]$^+$: 288.1964, found 288.1958.

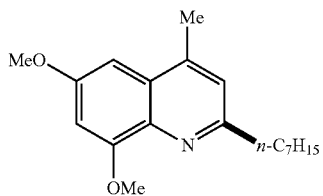

2-Heptyl-6,8-dimethoxy-4-methylquinoline (59)

Eluent: Hexane/ethyl acetate (10:1). Yield: 68%. Yellow solid. $^1$H NMR (500 MHz, CDCl$_3$) δ 7.15 (s, 1H), 6.73 (d, J=2.5 Hz, 1H), 6.70 (d, J=2.5 Hz, 1H), 4.03 (s, 3H), 3.93 (s, 3H), 2.93 (t, J=7.5, 2H), 2.60 (s, 3H), 1.81-1.74 (m, 2H), 1.45-1.38 (m, 2H), 1.37-1.31 (m, 2H), 1.30-1.25 (m, 4H), 0.88 (t, J=6.9 Hz, 3H). $^{13}$C NMR (126 MHz, CDCl$_3$) δ 159.3, 157.4, 156.5, 142.8, 136.2, 128.3, 123.0, 100.6, 93.6, 56.3, 55.6, 39.4, 31.9, 30.4, 29.9, 29.4, 22.8, 19.6, 14.2. HRMS (ESI) calcd for C$_{19}$H$_{28}$NO$_2$ [M+H]$^+$: 302.2122, found 302.2115.

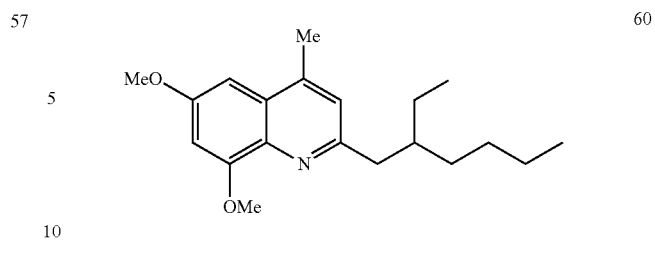

2-(2-Ethylhexyl)-6,8-dimethoxy-4-methylquinoline (60)

Eluent: Hexane/ethyl acetate (10:1). Yield: 32%. Yellow oil. $^1$H NMR (500 MHz, CDCl$_3$) δ 7.11 (s, 1H), 6.73 (d, J=2.5 Hz, 1H), 6.69 (d, J=2.5 Hz, 1H), 4.02 (s, 3H), 3.93 (s, 3H), 2.88 (d, J=7.3 Hz, 2H), 2.60 (s, 3H), 1.95-1.86 (m, 1H), 1.36-1.24 (m, 8H), 0.90-0.83 (m, 6H). $^{13}$C NMR (126 MHz, CDCl$_3$) δ 158.6, 157.4, 156.6, 142.3, 136.4, 128.3, 123.5, 100.7, 93.6, 56.4, 55.6, 43.5, 39.9, 32.6, 28.9, 25.9, 23.2, 19.6, 14.3, 10.9. HRMS (ESI) calcd for C$_{20}$H$_{30}$NO$_2$ [M+H]$^+$: 316.2280, found 316.2271.

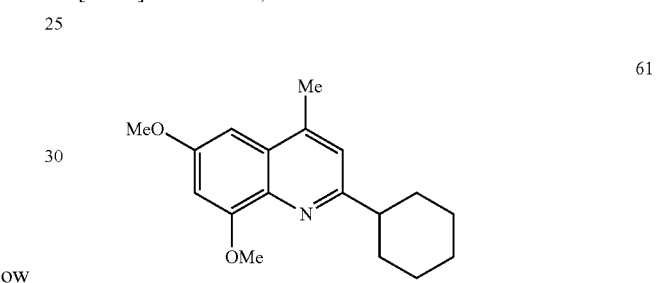

2-Cyclohexyl-6,8-dimethoxy-4-methylquinoline (61)

Eluent: Hexane/ethyl acetate (10:1). Yield: 72%. Yellow oil. $^1$H NMR (500 MHz, CDCl$_3$) δ 7.17 (s, 1H), 6.72 (d, J=2.5 Hz, 1H), 6.70 (d, J=2.5 Hz, 1H), 4.03 (s, 3H), 3.92 (s, 3H), 2.96 (tt, J=12.0, 3.4 Hz, 1H), 2.61 (s, 3H), 2.06-1.98 (m, 2H), 1.88-1.81 (m, 2H), 1.77 (dd, J=12.6, 1.3 Hz, 1H), 1.58-1.50 (m, 2H), 1.49-1.39 (m, 2H), 1.36-1.29 (m, 1H). $^{13}$C NMR (126 MHz, CDCl$_3$) δ 163.3, 157.5, 156.6, 142.9, 136.0, 128.6, 120.8, 100.6, 93.6, 56.4, 55.6, 47.7, 33.4, 26.6, 26.3, 19.7. HRMS (ESI) calcd for C$_{18}$H$_{24}$NO$_2$ [M+H]$^+$: 286.1807, found 286.1802.

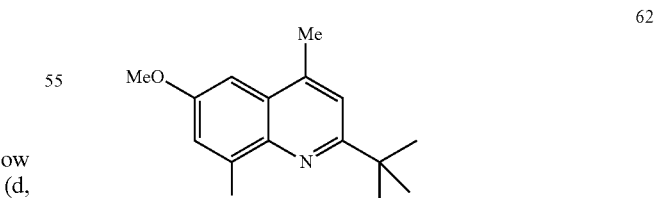

2-(tert-Butyl)-6,8-dimethoxy-4-methylquinoline (62)

Eluent: Hexane/ethyl acetate (10:1). Yield: 46%. Yellow solid. $^1$H NMR (500 MHz, CDCl$_3$) δ 7.35 (s, 1H), 6.73 (d, J=2.5 Hz, 1H), 6.69 (d, J=2.5 Hz, 1H), 4.03 (s, 3H), 3.93 (s, 3H), 2.62 (s, 3H), 1.46 (s, 9H). $^{13}$C NMR (126 MHz, CDCl$_3$) δ 165.4, 157.5, 156.9, 142.4, 135.6, 128.2, 120.2, 101.0, 93.6, 56.6, 55.5, 38.0, 30.4, 19.8. HRMS (ESI) calcd for C$_{16}$H$_{22}$NO$_2$ [M+H]$^+$: 260.1648, found 260.1645.

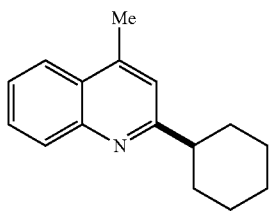

2-Cyclohexyl-4-methylquinoline (65)

Eluent: Hexane/ethyl acetate (10:1). Yield: 40%. Colorless oil. $^1$H NMR (500 MHz, CDCl$_3$) δ 8.04 (d, J=8.4 Hz, 1H), 7.94 (d, J=8.3 Hz, 1H), 7.66 (ddd, J=8.3, 6.9, 1.3 Hz, 1H), 7.52-7.46 (m, 1H), 7.16 (s, 1H), 2.87 (tt, J=12.1, 3.4 Hz, 1H), 2.68 (s, 3H), 2.03-2.00 (m, 2H), 1.93-1.86 (m, 2H), 1.83-1.76 (m, 1H), 1.62 (ddd, J=25.0, 12.5, 3.1 Hz, 2H), 1.53-1.42 (m, 2H), 1.39-1.31 (m, 1H). $^{13}$C NMR (126 MHz, CDCl$_3$) δ 166.7, 147.8, 144.3, 129.6, 129.0, 127.2, 125.5, 123.7, 120.4, 47.8, 33.0, 26.7, 26.3, 19.0.

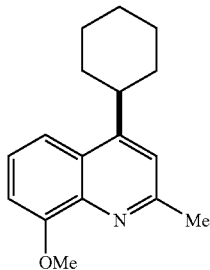

4-Cyclohexyl-8-methoxy-2-methylquinoline (66)

Eluent: Hexane/ethyl acetate (10:1). Yield: 50%. Colorless oil. $^1$H NMR (500 MHz, CDCl$_3$) δ 7.60 (d, J=8.4 Hz, 1H), 7.42-7.37 (m, 1H), 7.19 (s, 1H), 7.01 (d, J=7.3 Hz, 1H), 4.06 (s, 3H), 3.28-3.20 (m, 1H), 2.76 (s, 3H), 2.01-1.99 (m, 2H), 1.94-1.91 (m, 2H), 1.87-1.81 (m, 1H), 1.57-1.49 (m, 4H), 1.32-1.37 (m, 1H). $^{13}$C NMR (126 MHz, CDCl$_3$) δ 158.0, 155.6, 153.3, 140.2, 126.4, 125.2, 119.0, 114.9, 107.1, 56.1, 39.3, 33.7, 27.1, 26.5, 26.1. HRMS (ESI) calcd for C$_{17}$H$_{22}$NO [M+H]$^+$: 256.1697, found 256.1696.

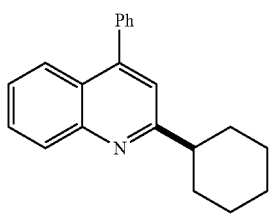

2-Cyclohexyl-4-phenylquinoline (67)

Eluent: Hexane/ethyl acetate (10:1). Yield: 52%. Colorless oil. $^1$H NMR (500 MHz, CDCl$_3$) δ 8.11 (d, J=8.4 Hz, 1H), 7.86 (dd, J=8.4, 0.9 Hz, 1H), 7.68 (ddd, J=8.3, 6.8, 1.4 Hz, 1H), 7.56-7.46 (m, 5H), 7.43 (ddd, J=8.2, 6.8, 1.2 Hz, 1H), 7.27 (s, 1H), 2.96 (tt, J=12.1, 3.4 Hz, 1H), 2.09-2.06 (m, 2H), 1.93-1.87 (m, 2H), 1.80-1.78 (m, 1H), 1.70-1.63 (m, 2H), 1.53-1.44 (m, 2H), 1.38-1.31 (m, 1H). $^{13}$C NMR (126 MHz, CDCl$_3$) δ 166.5, 148.8, 148.4, 138.7, 129.7, 129.5, 129.3, 128.6, 128.4, 125.8, 125.7, 125.7, 120.0, 47.8, 33.0, 26.7, 26.3. HRMS (APCI) calcd for C$_{21}$H$_{22}$N [M+H]$^+$: 288.1745, found 288.1747.

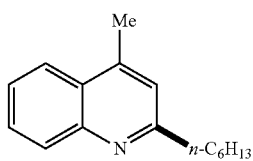

2-Hexyl-4-methylquinoline (68)

Eluent: Hexane/ethyl acetate (10:1). Yield: 38%. Yellow oil. $^1$H NMR (500 MHz, CDCl$_3$) δ 8.04 (d, J=8.4 Hz, 1H), 7.95 (dd, J=8.3, 0.8 Hz, 1H), 7.67 (ddd, J=8.3, 6.9, 1.3 Hz, 1H), 7.50 (ddd, J=8.1, 6.9, 1.1 Hz, 1H), 7.14 (s, 1H), 2.95-2.89 (m, 2H), 2.68 (s, 3H), 1.84-1.75 (m, 2H), 1.45-1.39 (m, 2H), 1.36-1.29 (m, 4H), 0.88 (t, J=7.1 Hz, 3H). $^{13}$C NMR (126 MHz, CDCl$_3$) δ 163.0, 147.9, 144.2, 129.5, 129.1, 126.9, 125.5, 123.7, 122.2, 39.5, 31.9, 30.2, 29.5, 22.7, 18.8, 14.2. HRMS (APCI) calcd for C$_{16}$H$_{22}$N [M+H]$^+$: 228.1750, found 228.1747.

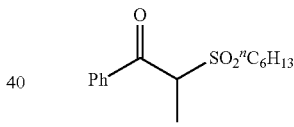

2-(Hexylsulfonyl)-1-phenylpropan-1-one

Eluent: Hexane/ethyl acetate (20:1). Yield: 78%.
Colorless oil. $^1$H NMR (500 MHz, CDCl$_3$) δ 8.02 (dd, J=8.4, 1.2 Hz, 2H), 7.66-7.59 (m, 1H), 7.50 (t, J=7.8 Hz, 2H), 4.99 (q, J=7.1 Hz, 1H), 3.18-3.01 (m, 2H), 1.89-1.76 (m, 2H), 1.71 (d, J=7.1 Hz, 3H), 1.45-1.35 (m, 2H), 1.29-1.27 (m, 4H), 0.86 (t, J=7.0 Hz, 3H). $^{13}$C NMR (126 MHz, CDCl$_3$) δ 193.9, 135.9, 134.4, 129.3, 129.0, 64.0, 49.1, 31.3, 28.3, 22.3, 20.5, 14.0, 13.5. HRMS (ESI) calcd for C$_{15}$H$_{22}$NaO$_3$S [M+Na]$^+$: 305.1190, found 305.1182.

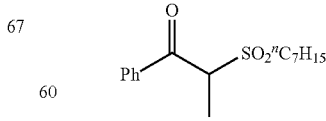

2-(Heptylsulfonyl)-1-phenylpropan-1-one

Eluent: Hexane/ethyl acetate (20:1). Yield: 80%. White solid. $^1$H NMR (500 MHz, CDCl$_3$) δ 8.03 (dd, J=8.4, 1.2 Hz, 2H), 7.68-7.61 (m, 1H), 7.52 (t, J=7.8 Hz, 2H), 4.99 (q, J=7.1 Hz, 1H), 3.19-3.02 (m, 2H), 1.87-1.79 (m, 2H), 1.73 (d, J=7.1 Hz, 3H), 1.41 (dd, J=15.2, 8.0 Hz, 2H), 1.36-1.23 (m, 6H), 0.87 (t, J=6.9 Hz, 3H). $^{13}$C NMR (126 MHz, CDCl$_3$) δ 194.0, 136.0, 134.6, 129.4, 129.1, 64.1, 49.1, 31.5, 28.9, 28.7, 22.6, 20.6, 14.1, 13.6. HRMS (ESI) calcd for C$_{16}$H$_{24}$NaO$_3$S [M+Na]$^+$: 319.1347, found 319.1338.

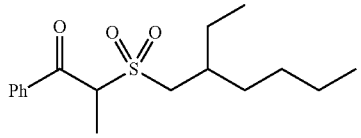 [SMILES: CCCCC(CC)CS(=O)(=O)C(C)C(=O)c1ccccc1]

2-((2-Ethylhexyl)sulfonyl)-1-phenylpropan-1-one

Eluent: Hexane/ethyl acetate (20:1). Yield: 73%. Colorless oil. $^1$H NMR (500 MHz, CDCl$_3$) δ 8.03 (dd, J=8.4, 1.2 Hz, 2H), 7.64 (t, J=7.4 Hz, 1H), 7.52 (t, J=7.8 Hz, 2H), 4.95 (q, J=7.1 Hz, 1H), 3.12 (ddd, J=13.7, 6.1, 4.8 Hz, 1H), 3.04-2.98 (m, 1H), 2.19-2.08 (m, 1H), 1.73 (d, J=7.1 Hz, 3H), 1.58-1.42 (m, 4H), 1.32-1.23 (m, 4H), 0.93-0.83 (m, 6H). $^{13}$C NMR (126 MHz, CDCl$_3$) δ 194.3, 136.1, 134.5, 129.4, 129.0, 64.8, 51.9, 33.1, 32.8, 28.3, 26.1, 22.8, 14.1, 13.7, 10.3. HRMS (ESI) calcd for C$_{17}$H$_{26}$NaO$_3$S [M+Na]$^+$: 333.1505, found 333.1495.

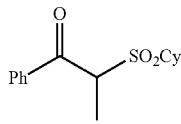

2-(Cyclohexylsulfonyl)-1-phenylpropan-1-one

Eluent: Hexane/ethyl acetate (20:1). Yield: 82%. White solid. $^1$H NMR (500 MHz, CDCl$_3$) δ 8.00 (d, J=7.5 Hz, 2H), 7.62 (t, J=7.4 Hz, 1H), 7.50 (t, J=7.7 Hz, 2H), 5.01 (q, J=7.1 Hz, 1H), 3.17 (tt, J=12.1, 3.4 Hz, 1H), 2.23-2.20 (m, 1H), 2.01-1.99 (m, 1H), 1.91-1.89 (m, 1H), 1.84-1.83 (m, 1H), 1.72 (d, J=7.1 Hz, 3H), 1.69-1.60 (m, 2H), 1.53-1.51 (m, 1H), 1.31-1.26 (m, 1H), 1.24-1.12 (m, 1H). 13C NMR (126 MHz, CDCl$_3$) δ 193.6, 136.0, 134.3, 129.1, 129.0, 62.1, 60.3, 25.4, 25.2, 25.1, 13.0. HRMS (ESI) calcd for C$_{15}$H$_{20}$NaO$_3$S [M+Na]$^+$: 303.1027, found 303.1025.

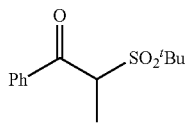

2-(tert-Butylsulfonyl)-1-phenylpropan-1-one

Eluent: Hexane/ethyl acetate (20:1). Yield: 86%. White solid. $^1$H NMR (500 MHz, CDCl$_3$) δ 8.02 (d, J=7.2 Hz, 2H), 7.62 (t, J=7.4 Hz, 1H), 7.51 (t, J=7.8 Hz, 2H), 5.08 (q, J=7.1 Hz, 1H), 1.77 (d, J=7.1 Hz, 3H), 1.44 (s, 9H). $^{13}$C NMR (126 MHz, CDCl$_3$) δ 193.1, 136.2, 134.1, 129.2, 129.0, 63.6, 60.0, 24.3, 14.7. HRMS (ESI) calcd for C$_{13}$H$_{18}$NaO$_3$S [M+Na]$^+$: 277.0868, found 277.0869.

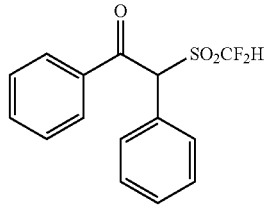

2-((Difluoromethyl)sulfonyl)-1,2-diphenylethan-1-one (3.54 g, 95%) was prepared and isolated by column chromatography as the brownish solid.

R$_f$=0.17 (Hex:EtOAc=8:2);

$^1$H NMR (400 MHz, CDCl$_3$) δ 7.90 (d, J=7.4 Hz, 2H), 7.60-7.55 (m, 3H), 7.44-7.40 (m, 5H), 6.72 (t, J=54.0 Hz, 1H), 6.38 (d, J=1.7 Hz, 1H);

$^{13}$C NMR (100 MHz, CDCl$_3$) δ 190.5, 134.8, 134.1, 130.9, 130.6, 129.7, 129.2, 129.1, 125.3, 115.2 (t, J=286.6 Hz), 73.9;

$^{19}$F NMR (377 MHz, CDCl$_3$) δ −121.60 (dd, J=276.7, 54.1 Hz, 1F), −122.81 (ddd, J=276.7, 53.8, 2.0 Hz, 1F);

Melting point 92.9-96.6° C.;

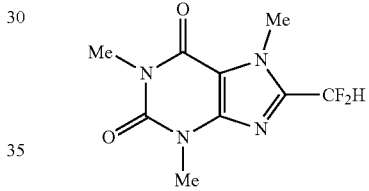

8-(Difluoromethyl)-1,3,7-trimethyl-3,7-dihydro-1H-purine-2,6-dione (1a, 20.5 mg, 84%) was prepared and isolated by preparative thin layer chromatography as the white powder. This compound is known and its characterization data are consistent with literature report.[1]

R$_f$=0.54 (Hex:EtOAc=2:8);

$^1$H NMR (500 MHz, CDCl$_3$) δ 6.77 (t, J=52.3 Hz, 1H), 4.18 (s, 3H), 3.59 (s, 3H), 3.44 (s, 3H);

$^{13}$C NMR (125 MHz, CDCl$_3$) δ 155.6, 151.4, 146.9, 142.8 (t, J=27.5 Hz), 109.8 (t, J=238.0 Hz), 109.5, 32.9, 29.8, 28.1;

$^{19}$F NMR (470 MHz, CDCl$_3$) δ −115.00 (d, J=52.3 Hz, 2F);

Melting point 168.6-167.8° C.;

GC-MS (EI) for C$_9$H$_{10}$F$_2$N$_4$O$_2$ Calcd: 244.1; Found: 244.1.

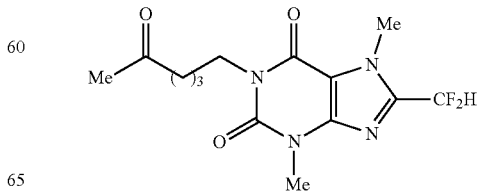

8-(Difluoromethyl)-3,7-dimethyl-1-(3-oxobutyl)-3,7-dihydro-1H-purine-2,6-dione (2b, 17.1 mg, 52%) was prepared and isolated by preparative thin layer chromatography as the colorless solid. This compound is known, and its characterization data are consistent with literature report.[1]

$R_f$=0.34 (Hex:EtOAc=1:1);

$^1$H NMR (500 MHz, Acetone-$d_6$) δ 6.76 (t, J=52.3 Hz, 1H), 4.16 (s, 3H), 4.03 (t, J=7.0 Hz, 2H), 3.57 (s, 3H), 2.52 (t, J=7.0 Hz, 2H), 2.16 (s, 3H), 1.68-1.66 (m, 4H);

$^{13}$C NMR (125 MHz, CDCl$_3$) δ 208.7, 155.4, 151.2, 147.0, 142.9 (t, J=27.4 Hz), 109.8 (t, J=238.0 Hz), 109.5, 43.1, 41.0, 32.9, 30.0, 29.7, 27.4, 20.9;

$^{19}$F NMR (470 MHz, CDCl$_3$) δ −114.98 (d, J=52.2 Hz, 2F);

GC-MS (EI) for $C_{14}H_{18}F_2N_4O_3$ Calcd: 328.1; Found: 328.2.

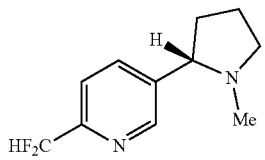

(S)-2-(Difluoromethyl)-5-(1-methylpyrrolidin-2-yl)pyridine (3b, 6.6 mg, 31%) was prepared and isolated by preparative thin layer chromatography as the colorless oil. This compound is known and its characterization data are consistent with literature report.[1]

$R_f$=0.23 (Hex:EtOAc=1:1);

$^1$H NMR (400 MHz, CDCl$_3$) δ 8.59 (s, 1H), 7.88 (dd, J=8.0, 1.6 Hz, 1H), 7.62 (d, J=8.0 Hz, 1H), 6.66 (t, J=55.6 Hz, 1H), 3.28 (t, J=8.8 Hz, 1H), 3.19 (t, J=8.3 Hz, 1H), 2.36 (q, J=9.0 Hz, 1H), 2.30-2.22 (m, 1H), 2.20 (s, 3H), 2.07-1.94 (m, 1H), 1.91-1.81 (m, 1H), 1.78-1.61 (m, 1H);

$^{13}$C NMR (100 MHz, CDCl$_3$) δ 151.7 (t, J=25.7 Hz), 149.1, 141.3, 136.1, 120.1 (t, J=2.9 Hz), 114.1 (t, J=239.9 Hz), 68.5, 57.0, 40.4, 35.4, 22.7;

$^{19}$F NMR (470 MHz, CDCl$_3$) δ −115.27 (d, J=55.8 Hz, 2F);

GC-MS (EI) for $C_{11}H_{14}F_2N_2$ Calcd: 212.2; Found: 212.1.

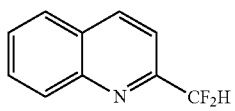 [SMILES: FC(F)c1ccc2ccccc2n1]

2-(Difluoromethyl)quinoline (4b, 10.4 mg, 58%) was prepared and isolated by preparative thin layer chromatography as the colorless oil. This compound is known and its characterization data are consistent with literature report.[2]

$R_f$=0.15 (Hex:EtOAc=9:1);

$^1$H NMR (500 MHz, Acetone-$d_6$) δ 8.93 (d, J=4.3 Hz, 1H), 8.10 (dd, J=8.5, 1.3 Hz, 1H), 8.05 (d, J=8.2 Hz, 1H), 7.76-7.72 (m, 1H), 7.63-7.60 (m, 2H), 7.42 (t, J=54.2 Hz, 1H);

$^{13}$C NMR (125 MHz, CDCl$_3$) δ 150.0, 148.6, 137.8, 130.4, 130.0, 127.8, 124.2, 123.3, 118.0 (t, J=7.7 Hz), 113.3 (t, J=240.6 Hz);

$^{19}$F NMR (470 MHz, CDCl$_3$) δ −115.09 (d, J=54.5 Hz, 2F);

GC-MS (EI) for $C_{10}H_7F_2N$ Calcd: 179.0; Found: 179.0.

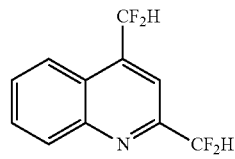

2,4-Bis(difluoromethyl)quinoline (4b', 6.6 mg, 29%) was prepared and isolated by preparative thin layer chromatography as the colorless oil. It was found that the volatility of this compound prevents precious quantification and yield presented here is determined based on the GC-MS. This compound is known and its characterization data are consistent with literature report.[2]

$R_f$=0.50 (Hex:EtOAc=9:1);

$^1$H NMR (500 MHz, CDCl$_3$) δ 8.27 (d, J=8.5 Hz, 1H), 8.17 (d, J=7.8 Hz, 1H), 7.95 (s, 1H), 7.89 (td, J=7.0, 1.4 Hz, 1H), 7.77 (td, J=7.7, 1.0 Hz, 1H), 7.22 (t, J=54.3 Hz, 1H), 6.83 (t, J=55.1 Hz, 1H);

a$^3$C NMR (125 MHz, CDCl$_3$) δ 152.6 (t, J=27.0 Hz), 147.6, 139.8 (t, J=22.0 Hz), 130.8, 130.7, 129.2, 124.7, 123.4, 114.2 (t, J=241.3 Hz), 114.2 (t, J=8.2 Hz), 113.0 (t, J=241.7 Hz);

$^{19}$F NMR (470 MHz, CDCl$_3$) δ −114.46 (d, J=54.6 Hz, 2F), −115.14 (d, J=54.3 Hz, 2F);

GC-MS (EI) for $C_{11}H_7F_4N$ Calcd: 229.1; Found: 229.0.

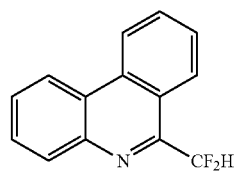

6-(Difluoromethyl)phenanthridine (5b, 11.0 mg, 48%) was prepared and isolated by preparative thin layer chromatography as the white solid. This compound is known, and its characterization data are consistent with literature report.[3]

$R_f$=0.48 (Hex:EtOAc=9:1);

$^1$H NMR (500 MHz, CDCl$_3$) δ 8.72 (d, J=8.4 Hz, 1H), 8.64-8.61 (m, 2H), 8.24-8.22 (m, 1H), 7.94 (td, J=7.7, 1.0 Hz, 1H), 7.83-7.77 (m, 4H); 13C NMR (125 MHz, CDCl$_3$) δ 151.4 (t, J=26.6 Hz), 142.5, 133.8, 131.2, 130.6, 129.1, 128.6, 127.8, 126.5 (t, J=4.2 Hz), 125.0, 122.4, 122.2, 118.4 (t, J=243.4 Hz);

$^{19}$F NMR (470 MHz, CDCl$_3$) δ −110.57 (d, J=56.3 Hz, 2F);

GC-MS (EI) for $C_{14}H_9F_2N$ Calcd: 229.0; Found: 229.1.

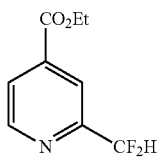

Ethyl 2-(difluoromethyl)isonicotinate (6b, 6.2 mg, 31%) was prepared and isolated by preparative thin layer chromatography as the colorless oil. This compound is known, and its characterization data are consistent with literature report.[2]

$R_f$=0.22 (Hex:EtOAc=9:1);
$^1$H NMR (500 MHz, CDCl$_3$) δ 8.83 (d, J=5.0 Hz, 1H), 8.21 (s, 1H), 8.00 (d, J=4.9 Hz, 1H), 6.72 (t, J=55.3 Hz, 1H), 4.47 (q, J=7.1 Hz, 2H), 1.45 (t, J=7.1 Hz, 3H);
$^{13}$C NMR (125 MHz, CDCl$_3$) δ 164.3, 153.9 (t, J=26.2 Hz), 150.4, 139.3, 124.7, 119.6 (t, J=3.1 Hz), 113.5 (t, J=240.9 Hz), 62.2, 14.2;
$^{19}$F NMR (470 MHz, CDCl$_3$) δ −116.02 (d, J=55.1 Hz, 2F);
GC-MS (EI) for C$_9$H$_9$F$_2$NO$_2$ Calcd: 201.1; Found: 201.1.

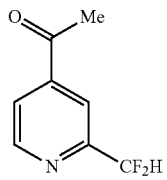

1-(2-(Difluoromethyl)pyridin-4-yl)ethan-1-one (7b, 6.0 mg, 35%) was prepared and isolated by preparative thin layer chromatography as the colorless oil. This compound is known, and its characterization data are consistent with literature report.[1]

$R_f$=0.17 (Hex:EtOAc=8:2);
$^1$H NMR (500 MHz, CDCl$_3$) δ 8.88 (d, J=5.0 Hz, 1H), 8.09 (s, 1H), 7.88 (d, J=5.0 Hz, 1H), 6.74 (t, J=55.3 Hz, 1H), 2.70 (s, 3H);
$^{13}$C NMR (125 MHz, CDCl$_3$) δ 196.3, 154.3 (t, J=26.4 Hz), 150.8, 144.2, 123.0, 118.0 (t, J=3.0 Hz), 113.5 (t, J=241.0 Hz), 26.7;
$^{19}$F NMR (470 MHz, CDCl$_3$) δ −115.99 (d, J=55.6 Hz, 2F);
GC-MS (EI) for C$_8$H$_7$F$_2$NO Calcd: 171.0; Found: 171.0.

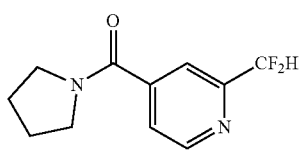 [SMILES: O=C(c1ccnc(C(F)F)c1)N1CCCC1]

(2-(Difluoromethyl)pyridin-4-yl)(pyrrolidin-1-yl)methanone (8b, 10.6 mg, 47%) was prepared and isolated by preparative thin layer chromatography as the colorless oil. This compound is new.

$R_f$=0.17 (Hex:EtOAc=1:1);
$^1$H NMR (500 MHz, CDCl$_3$) δ 8.74 (d, J=4.9 Hz, 1H), 7.74 (s, 1H), 7.51 (d, J=4.5 Hz, 1H), 6.67 (t, J=55.3 Hz, 1H), 3.67 (t, J=7.0 Hz, 2H), 3.40 (t, J=6.6 Hz, 2H), 2.03-1.91 (m, 4H);
$^{13}$C NMR (125 MHz, CDCl$_3$) δ 166.3, 153.4 (t, J=25.9 Hz), 150.0, 146.0, 123.0, 117.9 (t, J=2.9 Hz), 113.5 (t, J=241.0 Hz), 49.2, 46.4, 26.3, 24.3;
$^{19}$F NMR (470 MHz, CDCl$_3$) δ −116.20 (d, J=55.6 Hz, 2F);
GC-MS (EI) for C$_{11}$H$_{12}$F$_2$N$_2$O Calcd: 226.1; Found: 226.1.

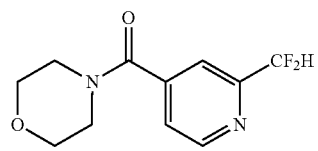 [SMILES: O=C(c1ccnc(C(F)F)c1)N1CCOCC1]

(2-(Difluoromethyl)pyridin-4-yl)(morpholino)methanone (9b, 11.1 mg, 46%) was prepared and isolated by preparative thin layer chromatography as the colorless oil. This compound is new.

$R_f$=0.13 (Hex:EtOAc=1:1);
$^1$H NMR (500 MHz, CDCl$_3$) δ 8.77 (d, J=4.9 Hz, 1H), 7.65 (s, 1H), 7.43 (d, J=4.8 Hz, 1H), 6.68 (t, J=55.3 Hz, 1H), 3.82 (bs, 4H), 3.66 (bs, 2H), 3.40 (bs, 2H);
$^{13}$C NMR (125 MHz, CDCl$_3$) δ 166.9, 153.7 (t, J=26.0 Hz), 150.2, 144.5, 123.0, 117.9 (t, J=3.0 Hz), 113.4 (t, J=241.2 Hz), 66.7, 47.9, 42.5;
$^{19}$F NMR (470 MHz, CDCl$_3$) δ −116.28 (d, J=55.5 Hz, 2F);
GC-MS (EI) for C$_{11}$H$_{12}$F$_2$N$_2$O$_2$ Calcd: 242.2; Found: 242.1.

12. The compound of claim 11, which is
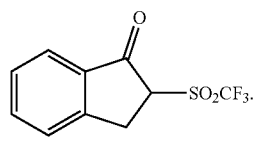

The invention claimed is:
1. A method for forming a compound of formula:

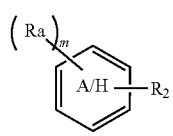

(II)

wherein

defines a mono or polycyclic aryl ring or a mono or polycyclic heteroaryl ring;
each Ra is independently selected from H or an optional substituent;
R$_2$ is CF$_3$, CF$_2$H, a linear alkyl of 2 or more carbon atoms, a branched alkyl of 3 or more carbon atoms or a cycloalkyl of 3 or more carbon atoms; and
m is an integer of 1 to 5;

comprising:

i) mixing together a compound of formula:

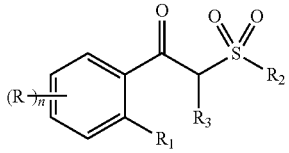
(I)

wherein $R_1$ is H, or an optional substituent;
$R_2$ is as defined above;
$R_3$ is H, or a C1-C6 linear alkyl, C3-C6 branched alkyl or C3-C6 cycloalkyl;
or $R_1$ and $R_3$, together with the atoms to which they are attached, form a 5-6 membered ring;
each R is independently selected from H or an optional substituent;
n is an integer of 1 to 4;
with compound of formula:

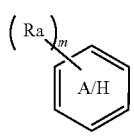
(III)

wherein

is as defined above, and Ra and m are as defined above;
ii) photo irradiating the mixture of step i) to provide said compound of formula (II).

2. The method of claim 1 wherein said aryl ring is a 6 membered monocyclic or 9-10 membered bicyclic benzenoid-type ring.

3. The method of claim 1 wherein said heteroaryl is monocyclic 5-6 membered or a 9-10 membered fused-bicyclic or 12-14 membered fused tricyclic ring.

4. The method of claim 1, wherein $R_1$ and $R_3$, together with the atoms to which they are attached, form a 5 membered ring or wherein $R_1$ is H and R3 is H, or a C1-C6 linear or C3-C6 branched alkyl.

5. The method of claim 1, wherein $R_2$ is $CF_2H$.

6. The method of claim 1, wherein the linear alkyl of group $R_2$ is an alkyl of 2 to 10 carbon atoms, wherein the branched alkyl of group $R_2$ is a branched alkyl of 3 to 8 carbon atoms and wherein the cycloalkyl of group $R_2$ is a cycloalkyl of 3 to 8 carbon atoms.

7. The method of claim 1, wherein R or Ra is each independently and each time selected from halogen, C1-6alkyl, C2-6alkenyl, C1-6 alkoxy, substituted C1-6 alkoxy, aryl, oxo (C=O), cyano (CN), —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl.

8. The method of claim 1, wherein R is H or C1-6alkyl.

9. The method of claim 1, wherein Ra is H, C1-6alkyl, C1-6 alkoxy, aryl, hydroxyl, or —C(O)OR40 wherein R40 and R41 are each independently H, or C1-6alkyl.

10. A method for forming a compound of formula:

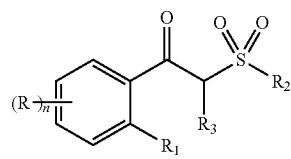
(I)

comprising:

1) reacting a compound of formula

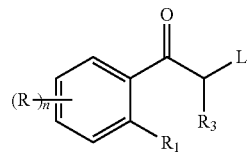
(IV)

with a compound of formula

$R_2$—S⁻X+ (V)

wherein $R_1$; $R_3$; R, and n are as defined in claim 1; and $R_2$ is a linear alkyl of 2 or more carbon atoms, a branched alkyl of 3 or more carbon atoms or a cycloalkyl of 3 or more carbon atoms;
L is a leaving group
X⁺ is a counterion;
to provide a compound of formula

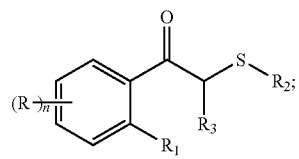
(VI)

wherein $R_1$; $R_2$; $R_3$; R, and n are as defined above; and 2) reacting said compound of formula (VI) with an oxidant to provide said compound of formula (I).

11. A compound of formula:

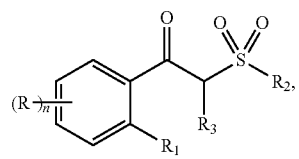

wherein
$R_2$ is $CF_3$, and
$R_1$ and $R_3$, together with the atoms to which they are attached, form a 5-6 membered ring.